United States Patent [19]

Nelson

[11] 4,154,950

[45] May 15, 1979

[54] 15-EPI-15-METHYL-16-PHENOXY-PGE COMPOUNDS

[75] Inventor: Norman A. Nelson, Galesburg, Mich.

[73] Assignee: The Upjohn Company, Kalamazoo, Mich.

[21] Appl. No.: 714,341

[22] Filed: Aug. 16, 1976

Related U.S. Application Data

[63] Continuation of Ser. No. 563,737, Mar. 31, 1975, abandoned.

[51] Int. Cl.$^2$ ............................................. C07C 177/00
[52] U.S. Cl. ........................................ 560/53; 560/55
[58] Field of Search ................................... 560/53, 55

[56] References Cited

U.S. PATENT DOCUMENTS 4,024,179  5/1977  Bindra et al. ........................... 560/53

FOREIGN PATENT DOCUMENTS 738554  10/1973  South Africa ........................... 260/473

*Primary Examiner*—Paul J. Killos
*Attorney, Agent, or Firm*—Robert A. Armitage

[57] ABSTRACT

Prostaglandin E-, $F_\alpha$-, $F_\beta$-, A-, and B-type compounds are disclosed with intermediates and with processes for making them. These compounds differ from the prostaglandins in that they are substituted at C-16 with a phenoxy or substituted phenoxy, and have a lower alkyl group in place of the hydrogen at C-15 and/or a lower alkoxy group in place of the hydroxy group at C-15. These compounds are useful for a variety of pharmacological purposes, including antiulcer, inhibition of platelet aggregation, increase in nasal patency, labor induction at term, and wound healing.

18 Claims, No Drawings

15-EPI-15-METHYL-16-PHENOXY-PGE COMPOUNDS

This is a continuation of application Ser. No. 563,737, filed Mar. 31, 1975, now abandoned.

BACKGROUND OF THE INVENTION

This invention relates to novel compositions of matter, to novel methods for producing said compositions, and to novel chemical intermediates useful in those processes. Particularly, this invention relates to certain novel analogs of some of the known prostaglandins which differ from the known prostaglandin in that they are substituted at C-16 with a phenoxy or substituted phenoxy, and have a lower alkyl group in place of the hydrogen at C-15 and/or a lower alkoxy group in place of the hydroxy at C-15. The known prostaglandins (PG's) include, for example, prostaglandin $E_1$ (PGE$_1$), prostaglandin $E_2$ (PGE$_2$), dihydroprostaglandin $E_1$ (dihydro-PGE$_1$), prostaglandin $F_{1\alpha}$ (PGF$_{1\alpha}$), prostaglandin $F_{2\alpha}$ (PGF$_{2\alpha}$), dihydroprostaglandin $F_{1\alpha}$ (dihydro-PGF$_{1\alpha}$), prostaglandin $F_{1\beta}$ (PGF$_{1\beta}$), dihydroprostaglandin $F_{1\beta}$ (dihydro-PGF$_{1\beta}$), prostaglandin $A_1$ (PGA$_1$), prostaglandin $A_2$ (PGA$_2$), dihydroprostaglandin $A_1$ (dihydro-PGA$_1$), prostaglandin $B_1$ (PGB$_1$), prostaglandin $B_2$ (PGB$_2$), and dihydroprostaglandin $B_1$ (dihydro-PGB$_1$). Each of the above-mentioned known prostaglandins is a derivative of prostanoic acid which has the following structure and carbon atom numbering:

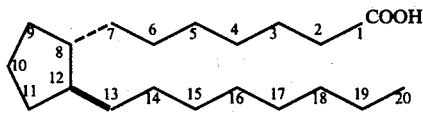

See, for example, Bergstrom et al., Pharmacol. Rev. 20, 1 (1968), and references cited therein. A systematic name for prostanoic acid is 7-[(2β-octyl)-cyclopent-1α-yl]heptanoic acid.

PGE$_1$ has the following structure:

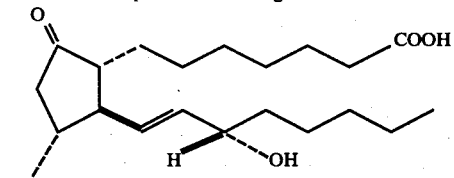

PGE$_2$ has the following structure:

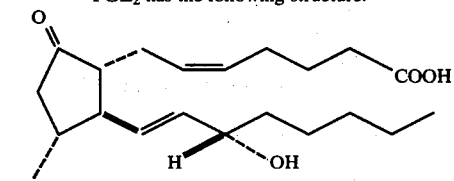

Dihydro-PGE$_1$ has the following structure:

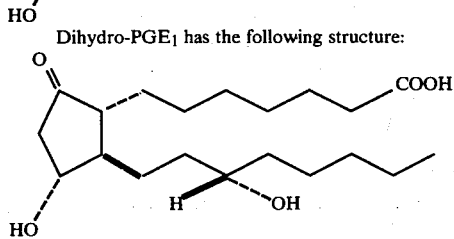

PGF$_{1\alpha}$ has the following structure:

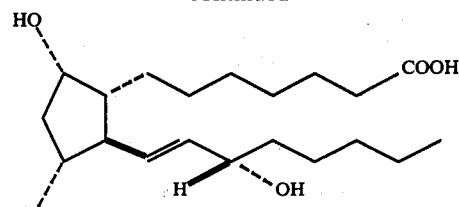

PGF$_{2\alpha}$ has the following structure:

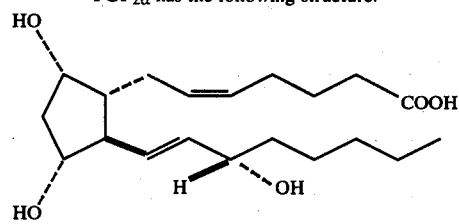

Dihydro-PGF$_{1\alpha}$ has the following structure:

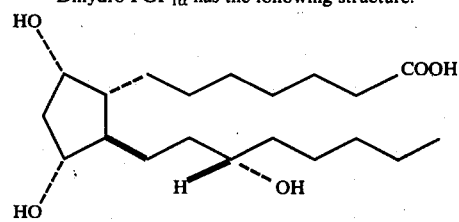

PGF$_{1\alpha}$ has the following structure:

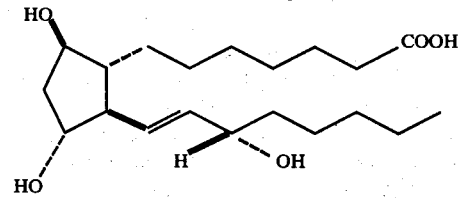

PGF$_{2\beta}$ has the following structure:

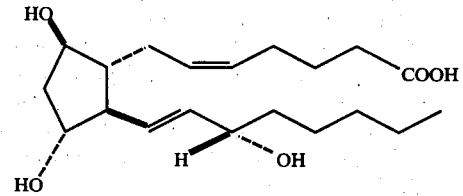

Dihydro-PGF$_{1\beta}$ has the following structure:

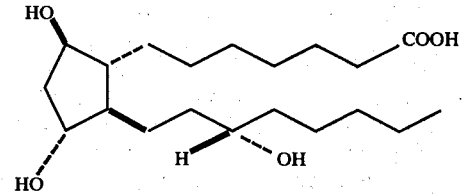

PGA$_1$ has the following structure:

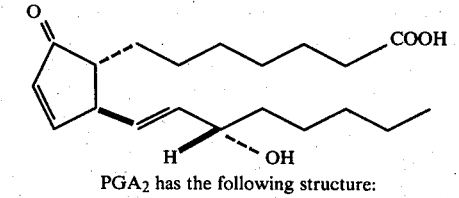

PGA$_2$ has the following structure:

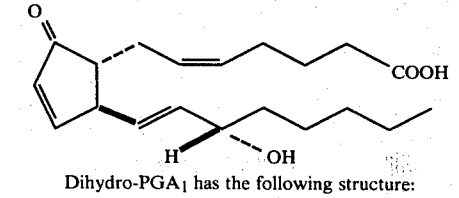

Dihydro-PGA$_1$ has the following structure:

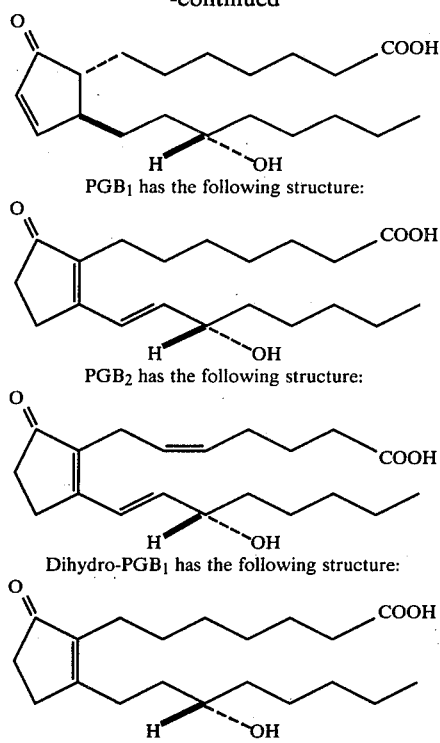

PGB₁ has the following structure:

PGB₂ has the following structure:

Dihydro-PGB₁ has the following structure:

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring.

The side-chain hydroxy at C-15 in the above formulas is in S configuration. See, Nature, 212, 38 (1966) for discussion of the stereochemistry of the prostaglandins. Expressions such as C-15, and the like, refer to the carbon atom in the prostaglandin or prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms, i.e., the dextrorotatory and levorotatory forms. As drawn, the above formulas each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin. For convenience hereinafter, use of the terms, PGE₁, PGE₂, and the like, refer to the optically active form of that prostaglandin with the same absolute configuration as PGE₁ obtained from mammalian tissues. When reference to the racemic form of one of those prostaglandins is intended, the word "racemic" or "dl" will procede the prostaglandin name.

PGE₁, PGE₂, dihydro-PGE₁, PGF₁α, PGF₂α, dihydro-PGF₁α, PGF₁β, PGF₂β, dihydro-PGF₁β, PGA₁, PGA₂, dihydro-PGA₁, PGB₁, PGB₂, dihydro-PGB₁, and their esters, acylates and pharmacologically acceptable salts, are extremely potent in causing various biological responses. For that reason, these compounds are useful for pharmacological purposes. See, for example, Bergstrom et al., Pharmacol. Rev. 20, 1 (1968) and references cited therein. A few of those biological responses are systemic blood pressure lowering in the case of the PGE and PGA compounds as measured, for example, in anesthetized (pentobarbital sodium) per olinium-treated rats with indwelling aortic and right heart cannulas; stimulation of smooth muscle as shown, for example, by tests on strips on guinea pig ileum, rabbit duodenum, or gerbil colon; potentiation of other smooth muscle stimulants; lipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decreasing blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments. Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGE, PGF$_\beta$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other antiasthmatic agents, such as sympathomimetics (isoproterenol, phenylephrine, epinephrine, etc.); xanthine derivatives (theophylline and aminophylline); and corticosteroids (ACTH and predinisolone). Regarding use of these compounds see M. E. Rosenthale, et al., U.S. Pat. No. 3,644,638.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, PGF$_\alpha$, and PGF$_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$_\alpha$, and PGF$_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, a PGE compound, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE and PGA compounds are useful as hypotensive agents to reduce blood pressure in mammals, including man. For this purpose, the compounds are administered by intravenous infusion at the rate about 0.01 to about 50 $\mu$g. per kg. of body weight per minute or in single or multiple doses of about 25 to 500 $\mu$g. per kg. of body weight total per day.

The PGE, PGF$_\alpha$, and PGF$_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, PGF$_\alpha$, and PGF$_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but no so old that regular ovulation has ceased. For that purpose the PG compound, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first or second trimester of the normal mammalian gestation period.

The PGE and PGF compounds are useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by PGE and PGF compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the PGE and PGF compounds are administered locally or systemically.

PGE$_2$, for example, is administered orally or vaginally at doses of about 5 to 50 mg. per treatment of an adult female human, with from one to five treatments per 24 hour period. PGE$_2$ is also administered intramuscularly or subcutaneously at doses of about one to 25 mg. per treatment. The exact dosages for these purposes depend on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 $\mu$g. per kg. of body weight or by intravenous infusion at a dose in the range of 0.1 to 20 $\mu$g. per kg. of body weight per minute until the desired effect is obtained. Subsequent doses are given by intravenous, intramuscular, or subcutaneous injection or infusion in the range 0.05 to 2 mg. per kg. of body weight per day.

The PGE and PGB compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 $\mu$g/ml. of the PGB compound or 1 to 500 $\mu$g/ml. of the PGE compound. Especially for topical use, these prostaglandins are useful in combination with antibiotics, for example, gentamycin, neomycin, polymixin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

The PGE, PGF$_\alpha$, PGF$_\beta$, PGA and PGB compounds are also useful in reducing the undesirable gastrointestinal effects resulting from systemic administration of anti-inflammatory prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including PGE$_1$, PGE$_2$, PGE$_3$, 13,14dihydro-PGE$_1$, and the corresponding 11-deoxy-PGE and PGA compounds. Prostaglandins are known useful in reducing the undersirable gastrointestinal effects resulting from systemic administration of indomethacin, phenylbutazone, and aspirin. These latter substances are specifically mentioned in Partridge et al. as non-steroidal anti-inflammatory agents. But these are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, or, alternatively, orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

Several compounds related to the novel compounds of this invention are known in the art.

See, for example, Netherlands Pat. No. 7,206,361, Derwent Farmdoc CPI No. 76383T-B, or Netherlands Pat. No. 7,306,462, Derwent Farmdoc CPI No. 73279U-B.

SUMMARY OF THE INVENTION

This invention provides novel prostaglandin analogs, esters of said analogs, lower alkanoates of said analogs and pharmacologically acceptable salts of said analogs.

This invention further provides novel intermediates useful in producing these compounds. This invention further provides novel processes for preparing these compounds.

The prostaglandin analogs of this invention can be represented by the formulas:

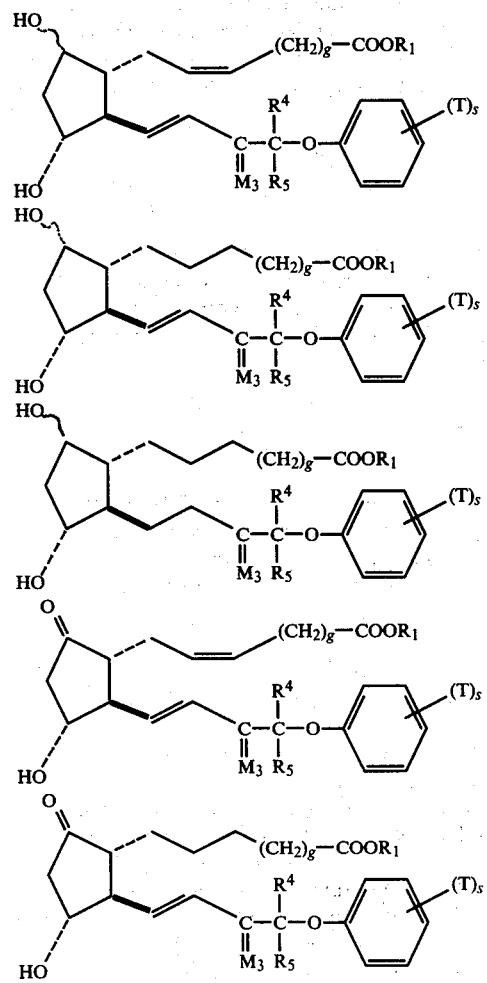

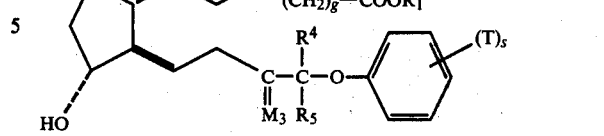

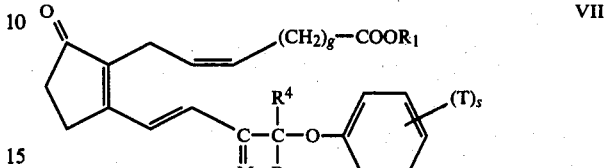

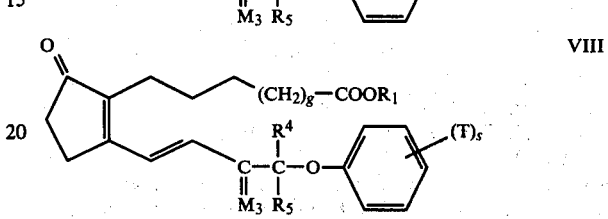

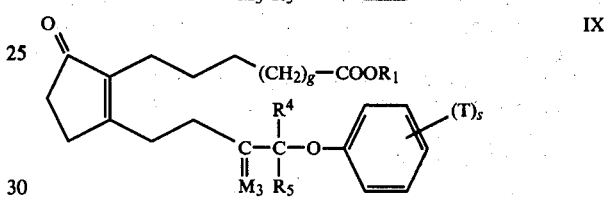

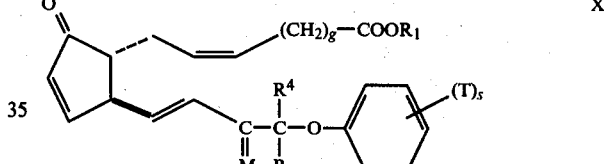

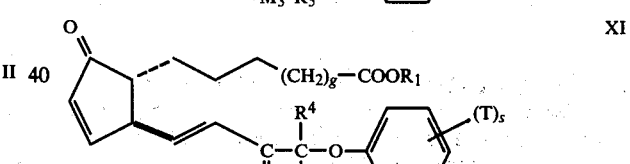

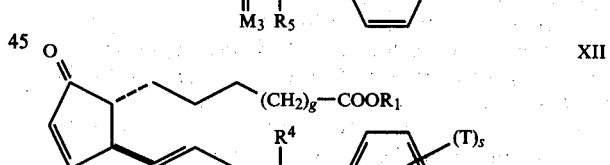

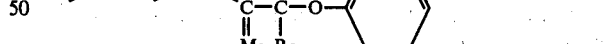

wherein $R_1$ is hydrogen alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive,

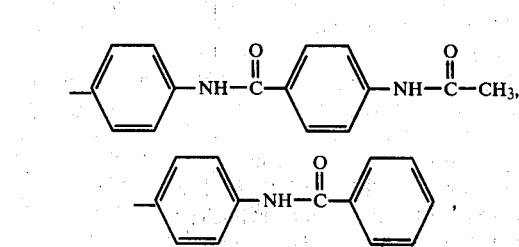

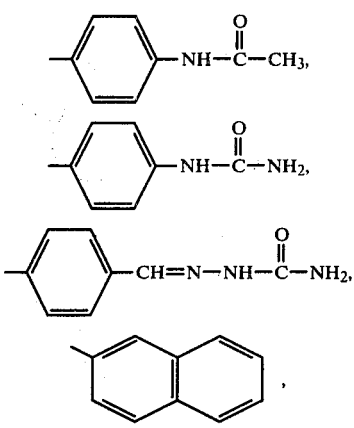

or a pharmacologically acceptable cation;

wherein T is alkyl of one to 3 carbon atoms, inclusive, fluoro, chloro, trifluoromethyl, or —OR$_2$ wherein R$_2$ is alkyl of one to 3 carbon atoms, inclusive, and wherein s is zero, one, 2, or 3, with the proviso that not more than two T's are other than alkyl, the T's being the same or different;

wherein R$_4$ and R$_5$ are hydrogen or alkyl of one to two carbon atoms, inclusive, being the same or different;

wherein M$_3$

or

wherein R$_7$ and R$_8$ are hydrogen or alkyl of 1 to 2 carbon atoms, inclusive, being the same or different, with the proviso that at least one of R$_7$ or R$_8$ must be alkyl of 1 to 2 carbon atoms, inclusive;

wherein g is 3 to 5, inclusive; and wherein ~ indicates the attachment of hydroxy to the cyclopentane ring in either the alpha or beta configuration.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl , 2,2-dimethylcyclohexyl, cycloheptyl, cyclooctyl, cyclononyl, and cyclodecyl.

Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

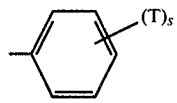

wherein T is alkyl of one to 3 carbon atoms, inclusive, fluoro, chloro, trifluoromethyl, or —OR$_2$ wherein R$_2$ is alkyl of one to 3 carbon atoms, inclusive; and s is zero, one, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2chloro-p-tolyl, (3-, 4-, 5-, or 6-)chloro-o-tolyl, 4-chloro-2-propylphenyl, 2-iosopropyl-4-chlorophenyl, 4-chloro-3,5-xylyl, (2,3-, 2,4-, 2,5-, 2,6- 3,4-, or 3,5-)dichlorophenyl, 4-chloro-3-fluorophenyl, (3-, or 4-)chloro-2-fluorophenyl, (o-, m-, p-)trifluoromethylphenyl, (o-, m-, or p-)methoxyphenyl, (o-, m-, or p-)ethoxyphenyl, (4- or 5-)chloro-2-methoxyphenyl, and 2,4-dichloro-(5- or 6-)methoxyphenyl.

Examples of the compounds within the scope of this invention are: 15-methyl-16-phenoxy-17,18,19,20-tetranor-PGF$_{2\alpha}$, a compound according to Formula I wherein ~ is alpha, g is 3, R$_1$ is hydrogen, M$_3$ is

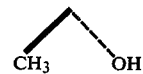

R$_4$ and R$_5$ are hydrogen and s is zero; 2a,2b-dihomo-15-epi-15-methyl-16-phenoxy-17,18,19,20-tetranor-PGE$_1$, methyl ester, 15-methyl ether, a compound according to formula VI wherein g is 5, or R$_1$ is methyl, M$_3$ is

R$_4$ and R$_5$ are hydrogen and s is 0; 13,14-dihydro-16-methyl, 16-(m-trifluoromethylphenoxy)-18,19,20-trinor-PGA$_1$, 15-methyl ether, a compound according to formula XII wherein g is 3, R$_1$ is hydrogen, M$_3$ is

R$_4$ and R$_5$ are both methyl, and (T)$_s$ is m-trifluoromethyl.

In the name of the novel prostaglandin analogs of this invention, "2a-homo" or "2a,2b-dihomo" indicates that one or two additional carbon atoms, respectively, have been inserted in the carboxy terminated side chain, specifically between the C-2 and C-3 carbon atoms. There are then 8 or 9 carbon atoms in that side chain instead of the normal 7 in the prostanoic acid structure.

From the end of the side chain they are identified as C-1, C-2, C-2a, C-2b, C-3, C-4, and C-5, and so on.

Also included in the compounds of this invention are the 15-alkyl prostaglandin analogs, for example 15-methyl and 15-ethyl. In naming these analogs "15-methyl" or "15-ethyl" is used when the hydrogen at position C-15 of the parent prostaglandins is replaced by a methyl or ethyl group, respectively.

Further included in the compounds of this invention are the 15-alkyl ethers, wherein $R_8$ is alkyl. For example, both 15-methyl ethers and 15-ethyl ethers are provided in this invention.

Also included within this invention are 15-epimeric compounds wherein $M_3$ is

and the C-15 hydroxy or alkoxy is in the β configuration. Hereinafter "15-epi" refers to the epimeric configuration.

In naming the compounds of this invention, "18,19,20-trinor" indicates the absence of 3 carbon atoms from the hydroxy-terminated side chain of the parent prostaglandins. Following the carbon atom numbering of the prostanoic acid structure, C-18, C-19, and C-20 are construed as missing, and the methylene at C-17 is replaced with the terminal methyl group. Likewise, 17,18,19,20-tetranor indicates the absence of the C-17, C-18, C-19 and C-20 carbon atoms from the methyl-terminated side chain. In this system of nomenclature the word "trinor" or "tetranor" in the name of the prostaglandin analog is construed as indicating 3 or 4 carbon atoms, respectively, are missing from the C-17 to C-20 position of the prostanoic acid carbon skeleton.

Accordingly there is provided a compound of the formula

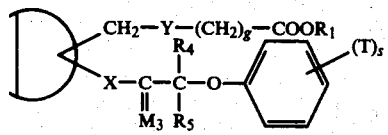

or a mixture comprising that compound and the enantiomer thereof, wherein (a) X is trans—CH=CH— or —CH₂CH₂— and Y is —CH₂CH₂— or (b) X is trans—CH=CH— and Y is cis—CH=CH—;

wherein D is one of the four carbocyclic moieties:

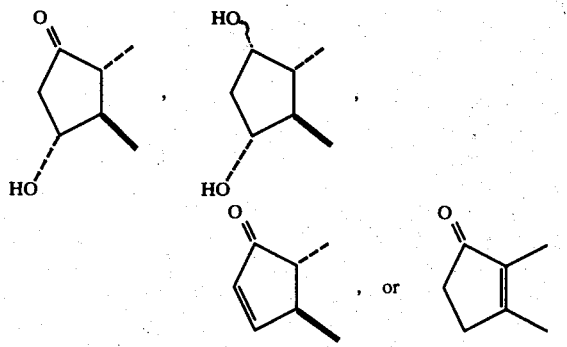

wherein ~ indicates attachment of hydroxyl to the ring in the alpha or beta configuration; and wherein g, $M_3$, $R_1$, $R_4$, $R_5$, T, and s are as defined above.

The preceding formula, which is written in generic form for convenience, represents PGE-thype compounds when D is

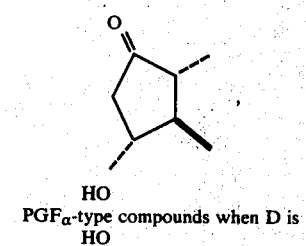

PGF$_\alpha$-type compounds when D is

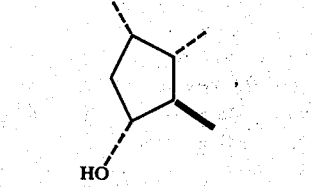

PGF$_\beta$-type compounds when D is

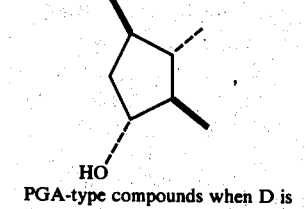

PGA-type compounds when D is

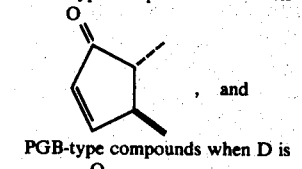

, and

PGB-type compounds when D is

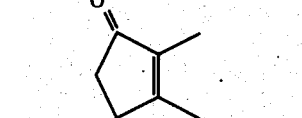

The novel compounds of this invention each cause the biological responses described above the the PGE, PGF$_\alpha$, PGF$_\beta$, PGA, and PGB compounds, respectively, and each of these novel compounds is accordingly useful for the above-described corresponding purposes, and is used for those purposes in the same manner as described above.

The known PGE, PGF$_\alpha$, PGF$_\beta$, PGA, and PGB compounds are all potent in causing multiple biological responses even at low doses. For example, PGE₁ and PGE₂ both cause vasodepression and smooth muscle stimulation at the same time they exert antilipolytic activity. Moreover, for many applications, these known prostaglandins have an inconveniently short duration of biological activity. In striking contrast, the novel prostaglandin analogs of this invention are substantially more selective with regard to potency in causing prostaglandin-like biological responses, and have a substantially longer duration of biological activity. Therefore, each of these novel prostaglandin analogs is surprisingly and unexpectedly more useful than one of the corresponding above-mentioned known prostaglandins for at least one of the pharmacological purposes indicated above for the latter, because it has a different and narrower spectrum of biological potency than the known prostaglandin, and therefore is more specific in its activity and causes smaller and fewer undesired side effects than when the known prostaglandin is used for the same purpose. Moreover, because of its prolonged activity, fewer and smaller doses of the novel prostaglandin analog can frequently be used to attain the desired result.

Another advantage of the novel compounds of this invention, especially the preferred compounds defined herein below, compared with the known prostaglandins, is that these novel compounds are administered effectively orally, sublingually, intravaginaly, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

As discussed above, the novel compounds of this invention are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the novel compounds of this invention by hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The novel prostaglandin analogs of this invention including their alkanoates, are used for the purposes described above in the free acid form, in ester form, in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal. When $R_1$ is not alkyl it is especially preferred that $R_1$ be one of the esters of the group represented by:

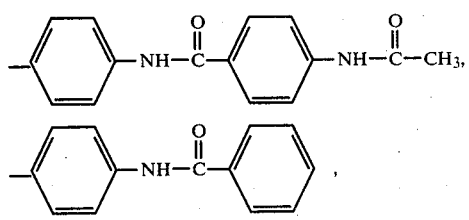

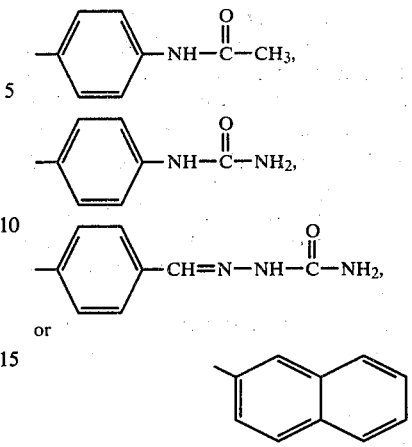

Pharmacologically acceptable salts of the novel prostaglandin analogs of this invention, compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylgycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The novel PG analogs of this invention are used for the purposes described above in free hydroxy form or also in the form wherein the hydroxy moieties are transformed to lower alkanoate moieties, e.g., —OH to —O-COCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

To obtain the optimum combination of biological response specificity, potency, and duration of activity, certain compounds within the scope of this invention are preferred.

Of the novel compounds of this invention, it is preferred that $R_4$ and $R_5$ be the same, both being either methyl or hydrogen. It is especially preferred that $R_4$ and $R_5$ both be hydrogen.

It is further preferred that g be either 3 or 5; that is, that the carboxy terminated side chain has either 7 or 9 carbon atoms, respectively. It is especially preferred that the carboxy terminated side chain have 7 carbon atoms that is, that g be 3. It is also preferred that only one of $R_7$ or $R_8$ be methyl and that the other of $R_7$ or $R_8$ be hydrogen.

It is further preferred that with respect to $(T)_s$ that s be zero or one and that when s is one T be trifluoromethyl, fluoro, or chloro.

The novel 16-phenoxy- or substituted phenoxy-PGE-, $PGF_\alpha$-, $PGF_\beta$-, PGA-, and PGB analogs of this invention are produced by the reactions and procedures described and exemplified hereinafter.

Reference to Charts A and B herein, will make clear the steps for preparing the certain prostaglandin-type intermediates useful in the preparation of the novel prostaglandin analogs of this invention.

Previously, the preparation of an intermediate bicyclic lactone diol of the formula

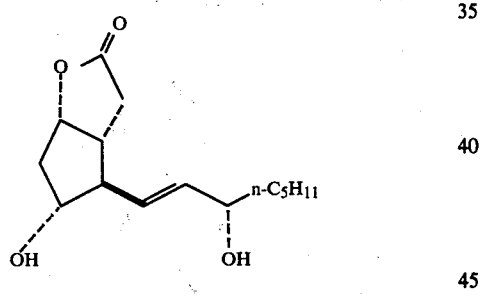

was reported by E. J. Corey et al., J. Am. Chem. Soc. 91, 5675 (1969), and later disclosed in an optically active form by E. J. Corey et al., J. Am. Chem. Soc. 92, 397 (1970). Conversion of this intermediate to $PGE_2$ and $PGF_{2\alpha}$, either in racemic or optically active form, was disclosed in those publications.

CHART A

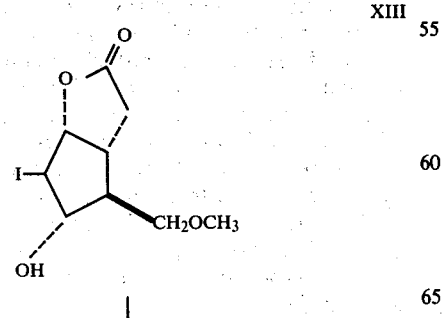

XIII

↓

XIV

-continued

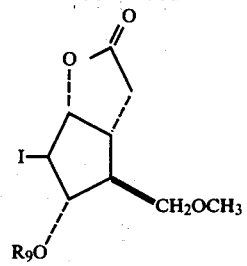

XV

↓

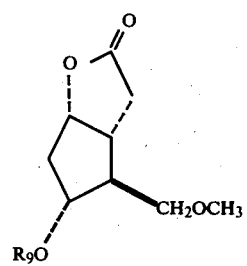

XVI

↓

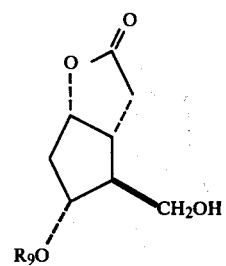

XVII

↓

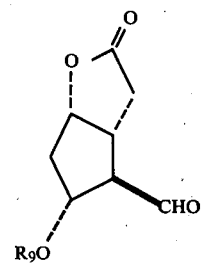

XVII

CHART B

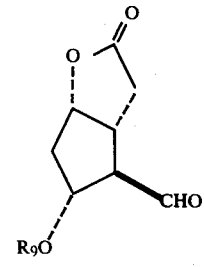

↓

XVIII

19
-continued

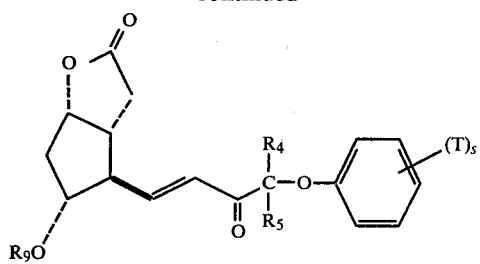

XIX

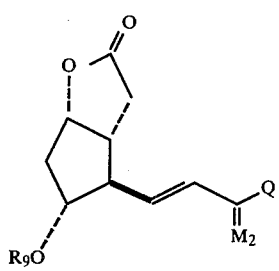

XX

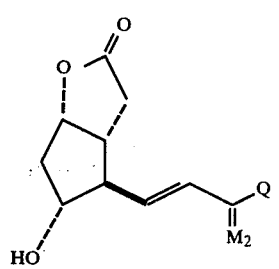

XXI

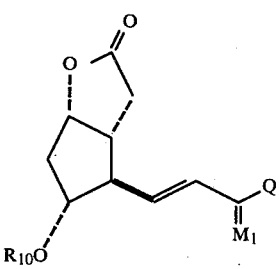

XXII

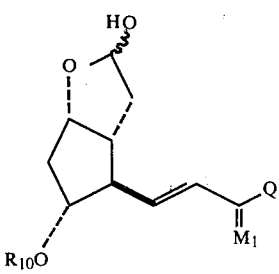

20
-continued

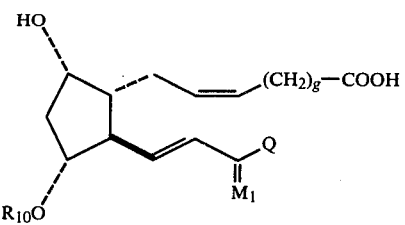

XXIII

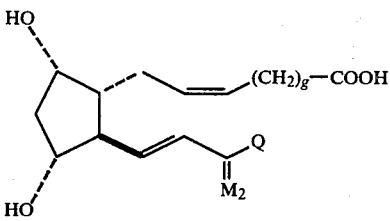

XXIV

The iodolactone of formula XIII of Chart A is known in the art (see Corey et al., above). It is available in either racemic or optically active (+ or −) form. For racemic products, the racemic form is used. For prostaglandins of natural configuration, the laevorotatory form (−) is used.

In Charts A and B, T, s, g, ~, $R_4$, and $R_5$ have the same meanings as defined above;

$M_2$ is

or

In Chart B, $M_1$ is

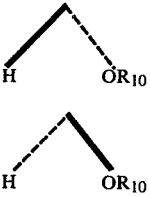

wherein $R_{10}$ is a blocking group, which is defined as any group which replaces hydrogen of the hydroxy groups, which is not attacked by nor is reactive to the reagents used in the respective transformation to the extent that the hydroxy group is, and which is subsequently replaceable by hydrogen at a later stage in the preparation of the prostaglandin-type products. Several blocking groups are known in the art, e.g. tetrahydropyranyl and substituted tetrahydropyranyl (see Corey, Proceedings of the Robert A. Welch Foundation Conferences on Chemical Research, XII, Organic Synthesis, pp. 51–79 (1969)). Those blocking groups which have been found useful include:

(1) tetrahydropyranyl;
(2) tetrahydrofuranyl; or
(3) a group of the formula

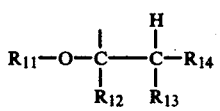

wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{12}$ and $R_{13}$ are the same or different, being hydrogen, alkyl of one to 4 carbon atoms, inclusive, phenyl or phenyl substituted with one, 2, or 3 alkyl of one to 4 carbon atoms, inclusive, or, when $R_{12}$ and $R_{13}$ are taken together, —$(CH_2)_a$— or —$(CH_2)_b$—O—$(CH_2)_c$— wherein a is 3, 4, or 5, b is one, 2, or 3, and c is one, 2, or 3 with the proviso that b plus c is 2, 3, or 4, and wherein $R_{14}$ is hydrogen or phenyl.

Further, in Chart B, Q is

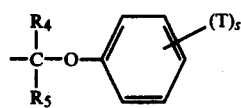

In Charts A and B, $R_9$ is an acyl protecting group. Those acyl protecting groups which have been found useful include:

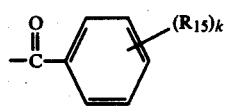

wherein $R_{15}$ is alkyl of one to 4 carbon atoms, inclusive, phenylalkyl of 7 to 10 carbon atoms, inclusive, or nitro, and k is zero to 5, inclusive, provided that not more than two $R_{15}$ are other than alkyl, and that the total number of carbon atoms in the $R_{15}$ does not exceed 10 carbon atoms;

wherein $R_{15}$ is as defined above, inclusive:

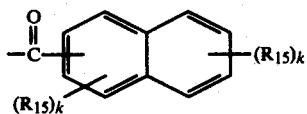

wherein $R_{15}$ and k are as defined above, being the same or different for each ring; or (4) acetyl.

In preparing the formula XIV compound by replacing the hydrogen of the hydroxyl group in the 3-position with the acyl group $R_9$, methods known in the art are used. Thus, an aromatic acid of the formula $R_9OH$, wherein $R_9$ is as defined above, for example benzoic acid, is reacted with the 3α-hydroxy compound in the presence of a dehydrating agent, e.g., carbonyl-bis-(imidazole), carbodiimides; or an anhydride of the aromatic acid of the formula $(R_9)_2O$, for example benzoic anhydride, is used.

Preferably, however, an acyl halide, e.g. $R_9Cl$, for example benzoyl chloride, is reacted with the formula XIII compound in the presence of a hydrogen chloride-scavenger, e.g. a tertiary amine such as pyridine, triethylamine, and the like. The reaction is carried out under a variety of conditions using procedures generally known in the art. Generally, mild conditions are employed, e.g. 20°–60° C., contacting the reactions in a liquid medium, e.g. excess pyridine or an inert solvent such as benzene, toluene or chloroform. The acylating agent is used either in stoichiometric amount or in excess.

As examples of $R_9$, the following are available as acids ($R_9OH$), anhydrides (($R_9)_2O$), or acyl chlorides ($R_9Cl$): benzoyl; substituted benzoyl, e.g. (2-, 3- or 4-)methylbenzoyl, (2-, 3-, or 4-)ethylbenzoyl, (2-, 3-, or 4-)isopropylbenzoyl, (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-)tolyl, (2-, 3-, or 4-)phenethylbenzoyl, 2-, 3-, or 4-nitrobenzoyl, (2,4- 2,5- or 3,5-)dinitrobenzoyl, 3,4-dimethyl-2-nitrobenzoyl, 4,5-dimethyl-2-nitrobenzoyl, 2-nitro-6-phenethylbenzoyl, 3-nitro-2-phenethylbenzoyl; mono-esterified phthaloyl, isophthaloyl, or terephthaloyl, (1- or 2-)naphthoyl; substituted naphthoyl, e.g. (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl. There may be employed, therefore, benzoyl chloride, 4-nitrobenzoyl chloride, 3,5-dinitrobenzoyl chloride, and the like, i.e. $R_9Cl$ compounds corresponding to the above $R_9$ groups. If the acyl chloride is not available, it is made from the corresponding acid and thionyl chloride as is known in the art. It is preferred that the $R_9OH$, $(R_9)_2O$, or $R_9Cl$ reactant does not have bulky, hindering substituents, e.g. tert-butyl, on both of the ring carbon atoms adjacent to the carbonyl attaching-site.

The formula-XV compound is next obtained by deiodination of XIV using a reagent which does not react with the lactone ring or the $OR_9$ moiety, e.g. zinc dust, sodium hydride, hydrazine-palladium, hydrogen and Raney nickel or platinum, and the like. Especially preferred is tributyltin hydride in benzene at about 25° C. with 2,2'-azobis(2-methylpropionitrile) as initiator.

The formula-XVI compound is obtained by demethylation of XV with a reagent that does not attack the $OR_9$ moiety, for example boron tribromide or trichloride. The reaction is carried out preferably in an inert solvent at about 0°–5° C.

The formula-XVII compound is obtained by oxidation of the —$CH_2OH$ of XVI to —CHO, avoiding decomposition of the lactone ring. Useful for this purpose are dichromate-sulfuric acid, Jones reagent, lead tetraacetate, and the like. Especially preferred is Collins' reagent (pyridine-$CrO_3$) at about 0°–10° C.

The formula-XVIII compound is obtained by Wittig alkylation of XVII, using the sodio derivative of the appropriate 2-oxo-3-phenoxy (or 3-substituted phenoxy)-alkylphosphonate. The trans enone lactone is obtained stereospecifically (see D. H. Wadsworth et al., J. Org. Chem. Vol. 30, p. 680 (1965)).

In preparing the formula-XVIII compounds of Chart B, certain phosphonates are employed in the Wittig reaction. These are of the general formula

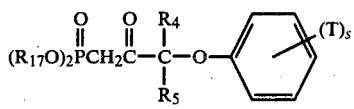

wherein $R_4$ and $R_5$ are hydrogen, methyl, or ethyl, being the same or different; $R_{17}$ is alkyl of one to 8 carbon atoms, inclusive; T is alkyl of one to 3 carbon atoms, inclusive, fluoro, chloro, trifluoromethyl, or —$OR_8$, wherein $R_8$ is alkyl of one to 3 carbon atoms, inclusive, and s is zero, one, 2, or 3, with the proviso that not more than two T's are other than alkyl, the T's being the same or different.

As examples of phosphonates useful for this purpose there are:

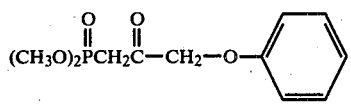

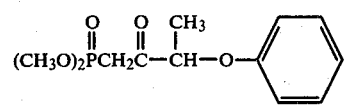

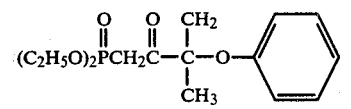

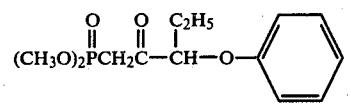

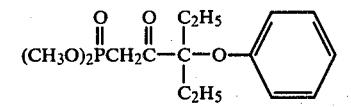

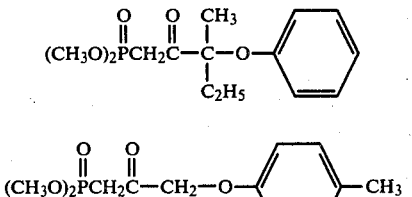

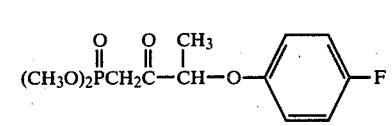

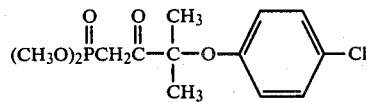

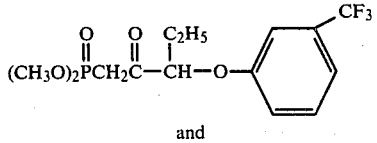

and

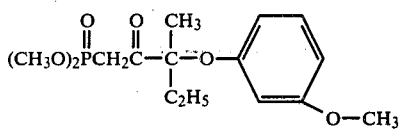

The phosphonates are prepared and used by methods known in the art. See Wadsworth et al., reference cited above. Conveniently, the appropriate aliphatic acid ester is condensed with the anion of dimethyl methylphosphonate produced by n-butyllithium. For this purpose, acids of the general formula

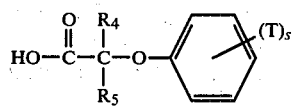

are used in the form of their lower alkyl esters, preferably methyl or ethyl. The methyl esters, for example, are readily formed from the acids by reaction with diazomethane. These aliphatic acids of various chain length, with phenoxy or substituted-phenoxy substitution within the scope of

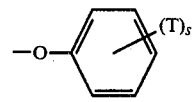

as defined above are known in the art or can be prepared by methods known in the art.

Many phenoxy-substituted acids are readily available, e.g. where $R_4$ and $R_5$ are both hydrogen: phenoxy-, (o-, m-, or p-)tolyloxy-, (o-, m-, or p-)ethylphenoxy-, 4-ethyl-o-tolyloxy-, (o-, m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-)chlorophenoxy-, (2,3-, 2,4-, 2,5-, 2,6-, 3,4-, or 3,5-)dichlorophenoxy-, $\alpha,\alpha,\alpha$-trifluoro-(o-, m-, or p-)tolyloxy-, or (o-, m-, or p-)methoxyphenoxyacetic acid; where $R_4$ is methyl and $R_5$ is hydrogen: 2-phenoxy-, 2-(o-, m-, or p-)tolyloxy-, 2-(3,5-xylyloxy)-, 2-(p-fluorophenoxy)-, 2-[(o-, m-, or p-)chlorophenoxy]-, 2-[(2,3-, 2,4-, 2,5-, 2,6-, 3,4-, or 3,5-)dichlorophenoxy]-, 2-[(4- or 6-)chloro-o-tolyloxy], or 2-($\alpha,\alpha,\alpha$-trifluoro-m-tolyloxy)-propionic acid; wherein $R_4$ and $R_5$ are both methyl: 2-methyl-2-phenoxy-, 2-[(o-, m-, or p-)chlorophenoxy]-2-methyl-, or 2-[(2,3-, 2,4-, 2,5-, 2,6-, 3,4-, or 3,5-)dichlorophenoxy]-2-methylpropionic acid; where $R_4$ is ethyl and $R_5$ is hydrogen: 2-phenoxy-, 2-[(o-, m-, or p-)fluorophenoxy]-, 2-[(o-, m-, or p-)chlorophenoxy]-, 2-[(2,3-, 2,4-, 2,5-, 2,6-, 3,4-, or 3,5-)dichlorophenoxy]-, or 2-(2-chloro-4-fluorophenoxy)butyric acid; wherein $R_4$ is ethyl and $R_5$ is methyl: 2-methyl-2-phenoxy- or 2-[(o-, m-, or p-)chlorophenoxy]-2-methylbutyric acid.

Other phenoxy substituted acids are available by methods known in the art, for example, by the Williamson synthesis of ethers using an alpha-halo aliphatic acid or ester with sodium phenoxide or a substituted sodium phenoxide. Thus, for example, the methyl ester of 2-)o-methoxyphenoxy)-2-methylbutyric acid is obtained by the following reaction:

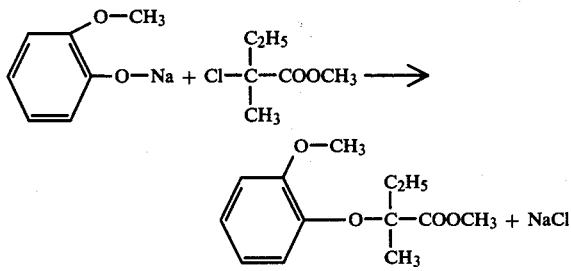

The reaction proceeds smoothly with heating and the product is recovered in the conventional way. The methyl ester is used for preparing the corresponding phosphonate as discussed above.

Alternatively, the phosphonate is prepared from an aliphatic acyl halide and the anion of a dialkyl methylphosphonate. Thus, 2-methyl-2-phenoxypropionyl chloride and dimethyl methylphosphonate yield dimethyl 2-oxo-3-methyl-3-phenoxybutylphosphonate. The acyl halides are readily available from the aliphatic acids by methods known in the art, e.g. chlorides are conveniently prepared using thionyl chloride.

Continuing with Chart B, the formula-XIX compound is obtained as a mixture of alpha and beta isomers by reduction of XVIII. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy)aluminum hydride, metal trialkoxy borohydrides, e.g., sodium trimethoxyborohydride, lithium borohydride, diisobutyl aluminum hydride, and when carbon-carbon double bond reduction is not a problem, the boranes, e.g., disiamylborane (bis-3-methyl-2-butylborane).

For production of natural-configuration PG-type compounds, the desired 15-alpha form of the formula-XIX compound is separated from the 15-beta isomer by silica gel chromatography.

The formula-XX compound is then obtained by deacylation of XIX with an alkali metal carbonate, for example, potassium carbonate in methanol at about 25° C.

When the blocking group $R_{10}$ is tetrahydropyranyl, the bis(tetrahydropyranyl ether) XXI is obtained by reaction of the formula-XX diol with 2,3-dihydropyran in an inert solvent, e.g., dichloromethane, in the presence of an acid condensing agent such as p-toluenesulfonic acid or pyridine hydrochloride. The dihydropyran is used in excess, preferably 4 to 10 times the stoichiometric amount. The reaction is normally complete in 1-10 hr. at 20°-50° C. When the blocking group is tetrahydrofuranyl, 2,3-dihydrofuran is used instead. When the blocking group is of the formula

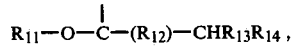

as defined above, the appropriate reagent is a vinyl ether, e.g. isobutyl vinyl ether or any vinyl ether of the formula

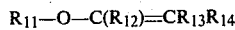

wherein $R_{11}$, $R_{12}$, $R_{13}$, and $R_{14}$ are as defined above; or an unsaturated cyclic or heterocyclic compound, e.g. 1-cyclohexen-1-yl methyl ether or 5,6-dihydro-4-methoxy-2H-pyran. See C. B. Reese et al., J. Am. Chem. Soc. 89, 3366 (1967). The reaction conditions for such vinyl ethers and unsaturated compounds are similar to those for dihydropyran above.

The lactol XXII is obtained on reduction of the formula-XXI lactone without reducing the 13,14-ethylenic group. For this purpose, diisobutylaluminum hydride is used. The reduction is preferably done at $-60°$ to $-70°$ C. The 15$\beta$-epimer of the formula-XXI lactone is readily obtained by the steps of Chart B, using the 15$\beta$ isomer of formula XIX.

The formula-XXIII compound is obtained from the formula-XXII lactol by the Wittig reaction, using a Wittig reagent derived from the appropriate $\omega$-carboxyalkyltriphenylphosphonium bromide, $HOOC-CH_2-(CH_2)_g-P(C_6H_5)_3Br$, and sodio dimethylsulfinyl-carbanide. The reaction is conveniently carried out at about 25° C. This formula-XXIII compound serves as an intermediate for preparing either certain PGF$_{2\alpha}$-type or PGE$_2$-type intermediates (Chart C). The phosphonium compounds are known in the art or are readily available, e.g. by reaction of an $\omega$-bromoaliphatic acid with triphenylphosphine.

The formula-XXIV PGF$_{2\alpha}$-type intermediate is obtained on hydrolysis of the blocking groups from the formula-XXIII compound, e.g. with methanol-HCl, acetic acid/water/tetrahydrofuran, aqueous citric acid, or aqueous phosphoric acid tetrahydrofuran, preferably at temperatures below 55° C., thereby avoiding formation of PGA$_2$-type compounds as by-products. Reference to Chart C will make clear the preparation of certain PGE$_2$-type intermediates. The 11,15-diether of the PGF$_{2\alpha}$-type products represented by formula XXIII oxidized at the 9-hydroxy position, preferably with Jones reagent. Finally the blocking groups are replaced with hydrogen, by hydrolysis as in preparing the PGF$_{2\alpha}$-type intermediate of Chart B. In Chart C, the symbols g, $M_2$, Q, and $R_{10}$ have the same meanings as in Charts A and B.

CHART C

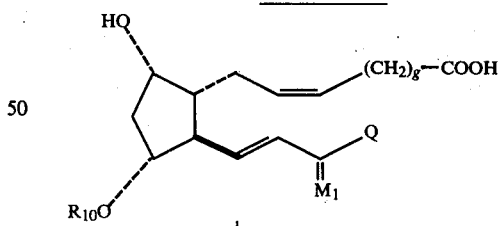

XXIII

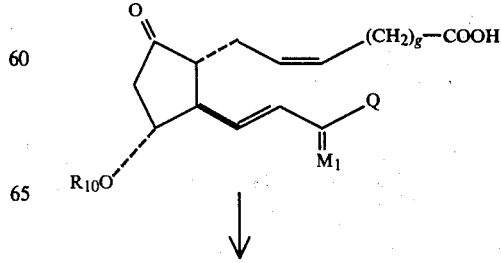

XXV

27

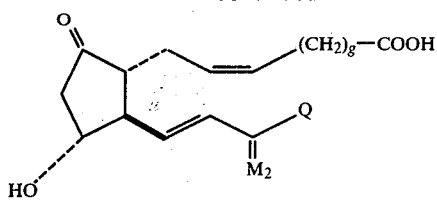

CHART D

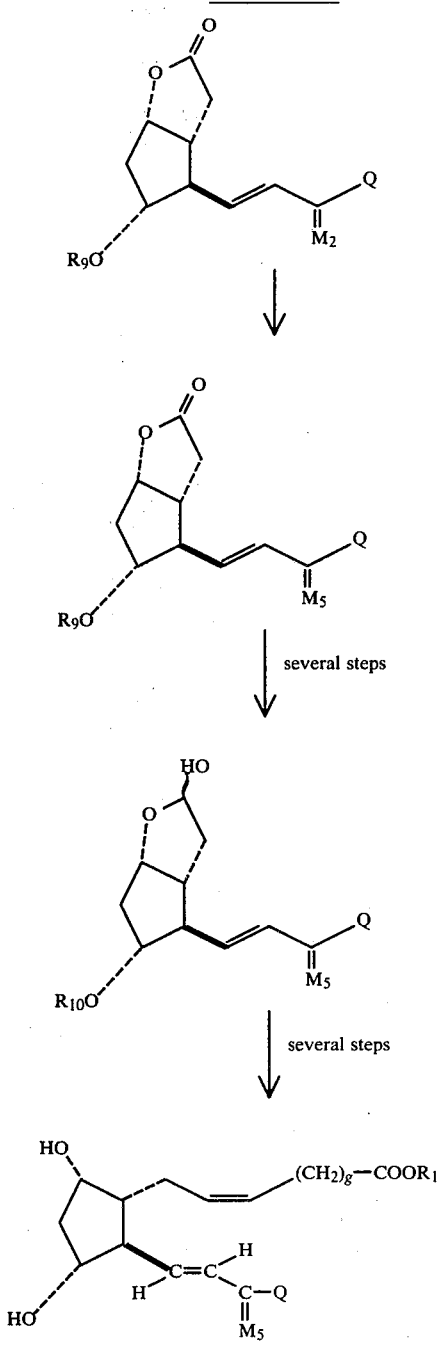

Referring to Chart D, there is shown the transformation of lactone XIX to 15-alkyl ether PGF-type products of formula-XXX. In Chart D, g, $M_2$, Q, $R_1$, $R_9$, $R_{10}$, and ~ have the same meanings as above. $M_6$ is either

28

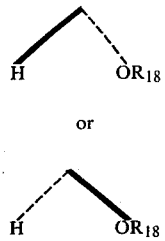

wherein $R_{18}$ is alkyl of one to 2 carbon atoms, inclusive. The starting materials are available from the steps of Chart B above or are readily available by methods known in the art.

The formula-XXVIII compound is prepared by alkylation of the side-chain hydroxy of the formula-XIX compound thereby replacing hydroxy with the $—OR_{18}$ moiety. For this purpose, diazoalkanes may be employed, preferably in the presence of a Lewis acid, e.g. boron trifluoride etherate, aluminum chloride, or fluoboric acid. When $R_{18}$ is methyl, diazomethane is used. See Fieser et al., "Reagents for Organic Synthesis", John Wiley and Sons, Inc., N.Y. (1967), p. 191. Other $—OR_{18}$ groups are formed by using the corresponding diazoalkane. For example diazoethane and diazomethane yield $—OC_2H_5$ and $—OCH_3$ respectively. The reaction is carried out by mixing a solution of the diazoalkane in a suitable inert solvent, preferably ethyl ether, with the formula-XIX compound. Generally the reaction proceeds at about 25° C. Diazoalkanes are known in the art or can be prepared by methods known in the art. See, for example, Organic Reactions, John Wiley and Sons, Inc., N.Y. Vol. 8. pp. 389–394 (1954).

Another method for the alkylation of the side chain hydroxy is by reaction with an alcohol in the presence of boron trifluoride etherate. Thus, methanol and boron trifluoride etherate yield the methyl ether wherein $R_{18}$ is methyl. The reaction is done at about 25° C. and is conveniently followed with thin layer chromatography (TLC).

Another method for the alkylation of the side-chain hydroxy is by the reaction of an alkyl halide, e.g. methyl iodide, in the presence of a metal oxide or hydroxide, e.g. barium oxide, silver oxide, or barium hydroxide. An inert solvent may be beneficial, for example benzene or dimethylformamide. The reactants are preferably stirred together and maintained at temperatures of 25°–75° C.

The formula-XXIX compound is then obtained in the conventional manner, for example by low temperature reduction with diisobutylaluminum hydride as discussed above for Chart B. The final 15-alkyl ether $PGF_\alpha$ product XXX is obtained from either XXVIII or XXIX by the same reactions and conditions discussed above for the steps of Chart B.

Further, by the method of Chart C the formula XXIX compound is transformed to the corresponding PGE-type compound of this invention.

Referring to Chart E, there is shown the transformation of lactone XVIII to lactol XXXIV useful for preparing 15-alkyl-PG-type products. In Chart E, Q, $R_4$, $R_5$, $R_{10}$, and ~ are as defined above for Chart B, $M_8$ is a mixture of

and

wherein $R_{19}$ is alkyl of one to 2 carbon atoms, inclusive, $M_7$ is a mixture of

and

wherein $R_{19}$ and $R_{10}$ are as defined above.

For the starting material XVIII refer to Chart B and the discussion pertaining thereto. Intermediate XXXI is obtained by replacing the side-chain oxo with $M_6$ by a conventional Grignard reaction, employing $R_{19}MgHal$. Next, the acyl group $R_9$ is removed by hydrolysis and the hydrogen atoms of the hydroxyl groups are replaced with blocking groups $R_{10}$ following the procedures of Chart B. Finally lactol XXXIV is obtained by reduction of lactone XXXIII in the same manner discussed above for Charts B and D.

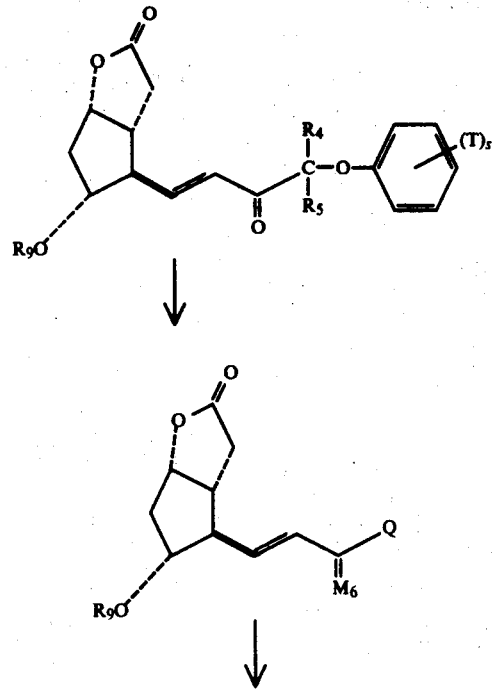

The 15-alkyl products of this invention are obtained from the formula-XXXIV lactol, following the procedures discussed above for Chart B. The 15-R and 15-S isomers are separated by conventional means, for example silica gel chromatography at either the lactone, lactol, or the final product stages.

Advantageously, separation techniques, such as high pressure liquid chromatography, are employed on PG-type, methyl ester products. In a similar fashion the corresponding PGE-type compounds are prepared from the formula-XXXIV compound using the procedures of Charts B and C.

Referring to Chart F, there is shown a convenient method for obtaining the 15-alkyl products from corresponding PGF-type intermediates shown broadly by formula XXXV. In Chart F, g, $M_1$, Q, $R_1$, $R_{19}$, Y, and ~ are as defined above. G is alkyl of one to 4 carbon atoms, inclusive, aralkyl of 7 to 12 carbon atoms, inclusive, phenyl, or phenyl substituted with one or 2 fluoro, chloro, or alkyl of one to 4 carbon atoms, inclusive, and $R_{20}$ is $R_1$ as defined above or silyl of the formula-Si-$(G)_3$ wherein G is as defined above. The various G's of a —Si$(G)_3$ moiety are alike or different. For example, a —Si$(G)_3$ can be trimethylsilyl, dimethyl(t-butyl)silyl, dimethylphenylsilyl, or methylphenylbenzylsilyl. Examples of alkyl of one to 4 carbon atoms, inclusive, are methyl, ethyl, propyl, isopropyl, butyl, isobutyl, sec-butyl, and tert-butyl. Examples of aralkyl of 7 to 12 carbon atoms, inclusive, are benzyl, phenethyl, α-phenylethyl, 3-phenylpropyl, α-naphthylmethyl, and 2-(β-naphthyl)ethyl. Examples of phenyl substituted with one or 2 fluoro, chloro, or alkyl of one to 4 carbon atoms, inclusive, are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

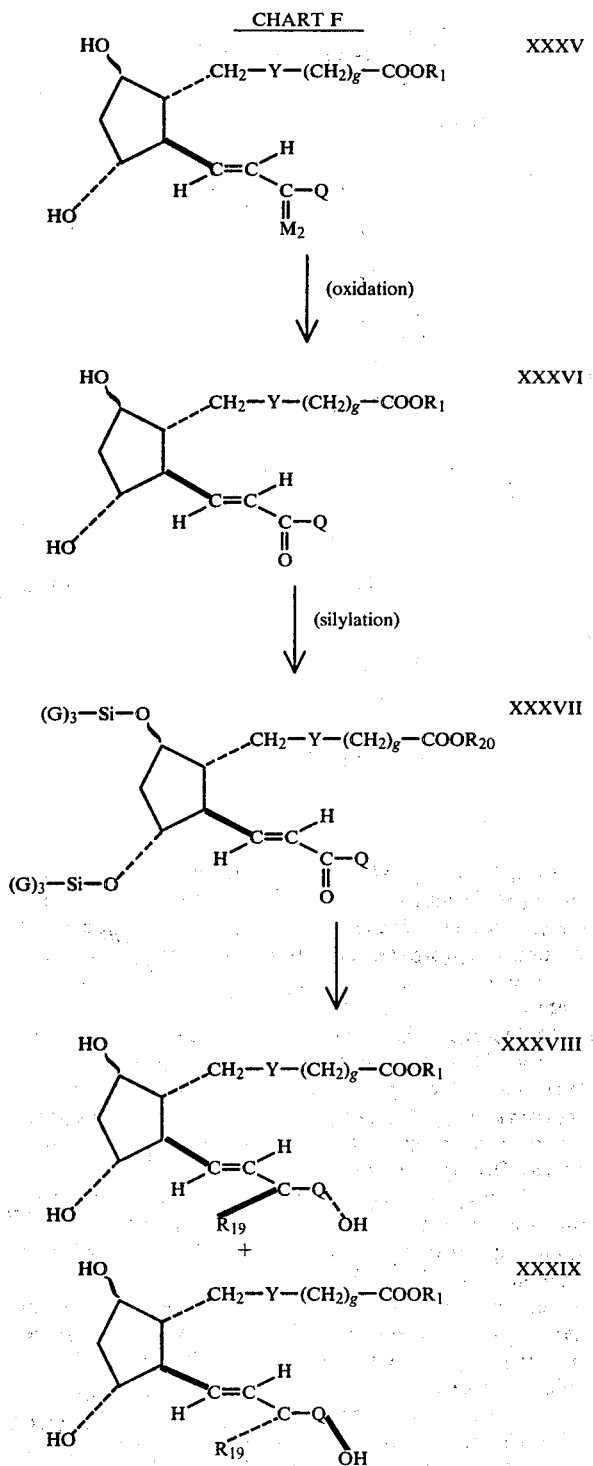

CHART F

This method is well-known for preparing 15-alkyl prostaglandins. See South African Pat. No. 2482, May 3, 1972, or Belgian Pat. No. 766,682, Derwent No. 72109S.

The acids and esters of formula XXXV, available herein by the processes of the preceding charts, are transformed to the corresponding intermediate 15-oxo acids and esters of formula XXXVI, respectively, by oxidation with reagents such as 2,3-dichloro-5,6-dicyano-1,4-benzoquinone, activated manganese dioxide, or nickel peroxide (see Fieser et al., "Reagents for Organic Synthesis," John Wiley and Sons, Inc., New York, N.Y., pp. 215, 637 and 731).

Continuing with Chart F, intermediate XXXVI is transformed to a silyl derivative of formula XXXVII by procedures known in the art. See, for example, Pierce, "Silylation of Organic Compounds," Pierce Chemical Co., Rockford, Ill. (1968). Both hydroxy groups of the formula-XXVI reactant are thereby transformed to —O—Si—(G)$_3$ moieties wherein G is as defined above, and sufficient of the silylating agent is used for that purpose according to known procedures. When R$_1$ in the formula-XXXVI intermediate is hydrogen, the —COOH moiety thereby defined is usually transformed to —COO—Si—(G)$_3$, additional silylating agent being used for this purpose. This latter transformation is aided by excess silylating agent and prolonged treatment. When R$_1$ in formula XXXVI is alkyl, then R$_{20}$ in formula XXXVII will also be alkyl. The necessary silylating agents for these transformations are known in the art or are prepared by methods known in the art. See, for example, Post, "Silicones and Other Silicon Compounds," Reinhold Publishing Corp., New York, N.Y. (1949).

The intermediate silyl compound of formula XXXVII is transformed to the final compounds of formula XXXVIII–XXXIX by first reacting the silyl compound with a Grignard reagent of the formula R$_{19}$MgHal wherein R$_{19}$ is defined as in Chart F, and Hal is chloro, bromo, or iodo. For this purpose, it is preferred that Hal be bromo. This reaction is carried out by the usual procedure for Grignard reactions, using diethyl ether as a reaction solvent and saturated aqueous ammonium chloride solution to hydrolyze the Grignard complex. The resulting disilyl or trisilyl tertiary alcohol is then hydrolyzed with dilute aqueous acetic acid. For this purpose, it is advantageous to use a diluent of water and sufficient of a water-miscible solvent, e.g., ethanol to give a homogenous reaction mixture. The hydrolysis is usually complete in 2 to 6 hours at 25° C., and is preferably carried out in an atmosphere of an inert gas, e.g., nitrogen or argon.

The mixture of 15-(S) and 15-(R) isomers obtained by this Grignard reaction and hydrolysis is separated by procedures known in the art for separating mixtures of prostanoic acid derivatives, for example, by high pressure liquid chromatography. In this instance, the lower alkyl esters, especially the methyl esters of a pair of 15(R) and 15(S) isomers are more readily separated by high pressure chromatography than are the corresponding acids. In this case, it is advantageous to esterify the mixture of acids as described below, separate the two esters, and then, if desired, saponify the esters by procedures known in the art for saponification of prostaglandins F.

Referring to Chart G, there is shown a preferred method of obtaining the 15-alkyl-PGF-type compounds as 15-alkyl ethers. In Chart G, g, M$_2$, M$_3$, M$_6$, Q, R$_1$, R$_{10}$, Y and ~ are as defined above. M$_8$ is either

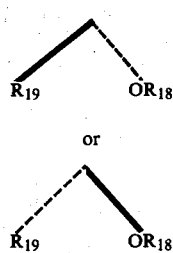

wherein $R_{18}$ and $R_{19}$ are as defined above, i.e. alkyl of one to 2 carbon atoms, inclusive, being the same or different. Starting material XXXV and intermediate XXXVI are identical with those of Chart F. Compound XL is obtained by replacing the hydrogen atoms of the C-9 and C-11 hydroxys with blocking groups $R_{10}$ by the methods discussed above for Chart B. Compound XLI is then obtained by replacing the C-15 oxo with $M_6$ by a Grignard reaction, employing $R_{19}MgHal$. Thereafter, a compound XLII is obtained by alkylation of the C-15 hydroxy using the methods and reagents discussed above for Chart D, for example diazoalkanes. Finally, the formula-XLII compound is readily transformed to the PGF-type products by hydrolysis of the $R_{10}$ blocking groups. The 15α and 15β isomers are separated by conventional means, for example high pressure liquid chromatography, as above.

Chart H shows a method whereby the novel $PGF_{2\alpha}$-type compounds of this invention are transformed into the corresponding novel $PGE_2$-type compounds of this invention.

CHART G

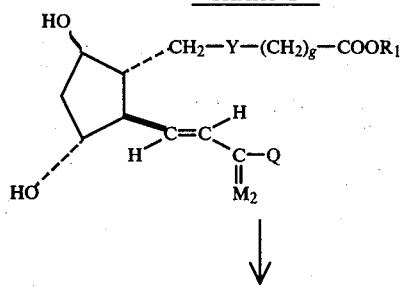

XXXV

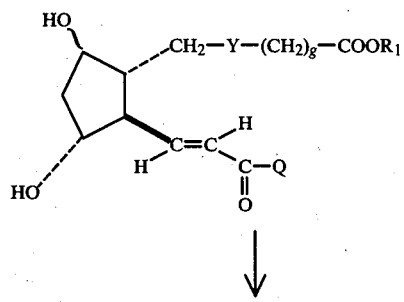

XXXVI

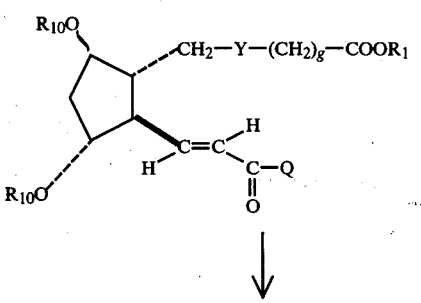

XL

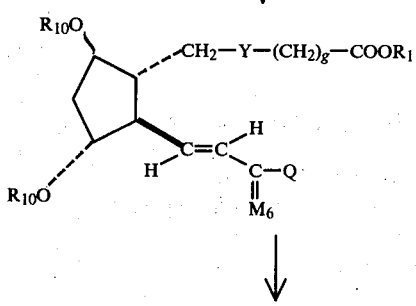

XLI

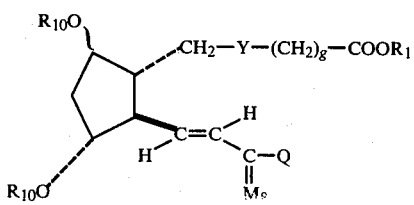

XLII

CHART H

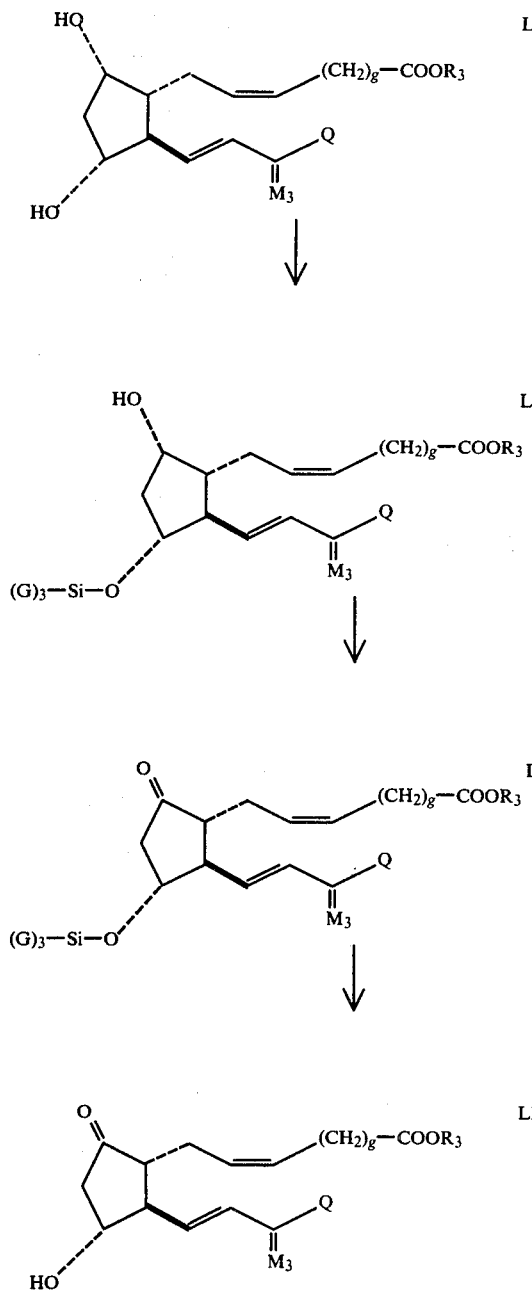

With reference to Chart H, $M_3$, Q, and g are as defined hereinabove. $R_3$ is hydrogen, alkyl of 1 to 12 carbon atoms inclusive, cycloalkyl of 3 to 10 carbon atoms, inclusive, aralkyl of 7 to 12 carbon atoms, inclusive, phenyl or phenyl substituted with 1, 2, or 3 chloro or alkyl of 1 to 4 carbon atoms, inclusive, and G is alkyl of 1 to 4 carbon atoms, inclusive, aralkyl of 17 to 12 carbon atoms, inclusive, phenyl, or phenyl substituted with 1 to 2 fluoro or chloro, or alkyl of 1 to 4 carbon atoms, inclusive, the various G's being the same or different.

The formula-LXXIII PGF$_{2\alpha}$-type compound is transformed by selective silylation into the formula-LXXIV 11-silyl derivative, by procedures known in the art. For a list of suitable silylation agents, see for reference Post, Silicones and Other Organic Compounds, Reinhold Publishing Company, New York, New York (1949). Procedures for this selective monosilylation are known in the art. See for reference U.S. Pat. No. 3,822,303.

The formula-LXXIV compound is then oxidized to form the formula-LXXV PGE$_2$-type compound by methods known in the art. By a preferred route the Collins' reagent is used to effect this oxidation by methods known in the art. See for reference J. C. Collins, et al., Tetrahedron Letters 3363 (1968).

The formula-LXXVI PGE$_2$-type compound is then produced by hydrolysis. This hydrolysis is effectively carried out under acidic conditions as is known in the art. For example, a diluent of water and a water miscible alcohol such as ethanol, is used to provide a homogeneous reaction mixture. The reaction proceeds to completion at 25° C. under a nitrogen or argon atmosphere in 2 to 6 hours.

By an optional route the PGF$_{2\alpha}$-type compounds of this invention are prepared from the corresponding lactone starting material using the procedure of the above charts, except that the use of blocking groups is omitted. Thus, by this optional route the lactol intermediates above are transformed to the free acid prostaglandin-type compounds of this invention by Wittig alkylation, without subsequent hydrolysis of any blocking groups.

The PGE$_1$- and 13,14-dihydro-PGE$_2$-type products of this invention are prepared by ethylenic reduction of the corresponding PGE$_2$-type compounds. Reducing agents useful for this transformation are known in the art. Thus, hydrogen is used at atmospheric pressure or low pressure with catalysts such as palladium on charcoal or rhodium on aluminum. See, for example, E. J. Corey et al., J. Am. Chem. Soc. 91, 5677 (1969) and B. Samuelsson, J. Biol. Chem. 239, 4091 (1964). For the PGE$_1$ type compounds, the reduction is terminated when one equivalent of hydrogen is absorbed; for the 13,14-dihydro-PGE$_1$ type compounds, when two equivalents are absorbed. For the PGE$_1$-type compounds it is preferred that a catalyst be used which selectively effects reduction of the cis-5,6-carbon-carbon double bond in the presence of the trans-13,14 unsaturation. Mixtures of the products are conveniently separated by silica gel chromatography.

Alternatively, the 11-mono- or 11,15-bis-silyl ethers of the PGE$_2$-type compounds (formula LXXV of Chart H) and reduced subsequently hydrolyzed to remove the silyl groups.

CHART I

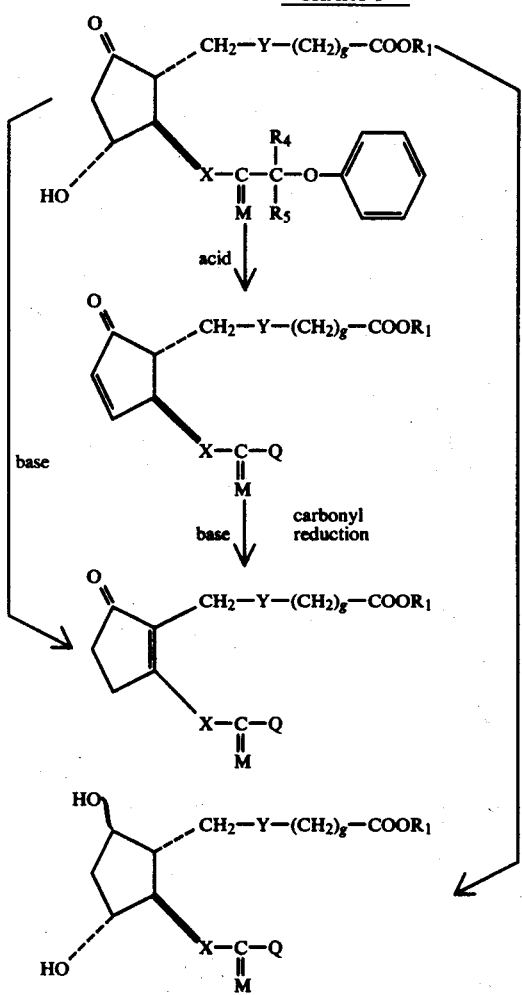

Chart I shows transformations from the novel PGE-type compounds to the corresponding PGF-, PGA-, and PGB-type compounds. In figures LXXVII, LXXVIII, LXXIX, and LX of Chart I, g, Q, and ~ have the same meanings as in Chart B; $R_1$ has the same meaning as in Chart D; M is

wherein $R_7$ and $R_8$ are hydrogen or alkyl of one to 2 carbon atoms, inclusive, being the same or different, with the proviso that at least one of $R_7$ or $R_8$ is alkyl of one to 2 carbon atoms, inclusive; and (a) X is trans-CH=CH— or —CH$_2$CH$_2$—, and Y is —CH$_2$CH$_2$—, or (b) X is trans-CH=CH— and Y is cis-CH=CH—. When X is trans-CH=CH— and Y is —CH$_2$CH$_2$—, formula LXXVII represents PGE$_1$ type compounds; when X is —CH$_2$CH$_2$— and Y is —CH$_2$CH$_2$—, formula LXXVII represents 13,14-dihydro-PGE$_1$ type compounds; and when X is trans-CH=CH— and Y is cis-CH=CH—, formula LXXVII represents PGE$_2$ type compounds. Thus, formulas LXXVII, LXXVIII, LXXIX, and LX embrace all of the novel compounds of this invention.

Thus, the various PGF$_\beta$-type compounds encompassed by formulas I, II, and III are prepared by carbonyl reduction of the corresponding PGE-type compounds, e.g. formulas IV, V, and VI.

These ring carbonyl reductions are carried out by methods known in the art for ring carbonyl reductions of known prostanoic acid derivatives. See, for example, Bergstrom et al., Arkiv Kemi 19, 563 (1963), Acta. Chem. Scand. 16, 969 (1962), and British Specification No. 1,097,533. Any reducing agent is used which does not react with carbon-carbon double bonds or ester groups. Preferred reagents are lithium(tri-tert-butoxy)aluminum hydride, the metal borohydrides, especially sodium, potassium and zinc borohydrides, the metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Greene et al., J. Lipid Research 5, 117 (1964). Alternatively useful as separation methods are partition chromatographic procedures, both normal and reversed phase, preparative thin layer chromatography, and countercurrent distribution procedures.

The various PGA-type compounds encompassed by formulas X, XI, and XII are prepared by acidic dehydration of the corresponding PGE-type compounds, e.g. formulas IV, V, and VI.

These acidic dehydrations are carried out by methods known in the art for acidic dehydrations of known prostanoic acid derivatives. See, for example, Pike et al., Proc. Nobel Symposium II, Stockholm (1966), Interscience Publishers, New York, pp. 162–163 (1967); and British Specification No. 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may cause partial hydrolysis of an ester reactant.

The various PGB-type compounds encompassed by formulas VII, VIII, and IX are prepared by basic dehydration of the corresponding PGE-type compounds encompassed by formulas IV, V, and VI or by contacting the corresponding PGA-type compounds encompassed by formulas X, XI, and XII with base.

These dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The PGE-type or PGA-type compound is maintained in such a reaction medium until no further PGB-type compound is formed, as shown by the characteristic ultraviolet light absorption near 278 $\mu$ for the PGB-type compound.

Optically active compounds are obtained from optically active intermediates according to the process steps of Charts A, B, D, and E. Likewise, optically active products are obtained by the transformations of optically active compounds following the processes of Charts C, F, G, and H. When racemic compounds are used in reactions corresponding to the processes of Charts A–H, inclusive, and racemic products are obtained, these racemic products may be used in their racemic form or, if preferred, they may be resolved as optically active isomers by procedures known in the art.

For example, when final compound I to XII is a free acid, the dl form thereof is resolved into the d and l forms by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acid of formula I to XII is then obtained by treatment of the salt with an acid by known general procedures.

As discussed above, the stereochemistry at C-15 is not altered by the transformations of Charts A and B; the 15$\beta$ epimeric products of formula XXIV are obtained from 15$\beta$ formula-XIX reactants. Another method of preparing the 15$\beta$ products is by isomerization of the PGF$_1$- or PGE$_1$-type compounds having 15$\alpha$ configuration, by methods known in the art. See, for example, Pike et al., J. Org. Chem. 34, 3552 (1969).

As discussed above, the processes herein described inclusive, lead variously to acids (R$_1$ is hydrogen) or to esters.

When the alkyl ester has been obtained and an acid is desired, saponification procedures, as known in the art for F-type prostaglandins may be used.

For alkyl esters of E-type prostaglandins enzymatic processes for transformation of esters to their acid forms may be used by methods known in the art. See for reference E. G. Daniels, Process for Producing An Esterase, U.S. Pat. No. 3,761,356.

When an acid has been prepared and an alkyl, cycloalkyl or aralkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively.

Similarly, diazocyclohexane and phenyldiazomethane yield cyclohexyl and benzyl esters respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

The phenyl and substituted phenyl esters of this invention are prepared by methods known in the art. For example, the prostaglandin-type free acid may be silylated by methods known in the art, thereby protecting the free hydroxy groups. Since the silylation often transforms the carboxy acid moiety, —COOH, into a silyl ester derivative, a brief treatment of the silylated compound with water may be necessary to transform the silylated compound into free acid form. This free acid may then be reacted with oxalyl chloride to provide an acid chloride. The acid chloride may be esterified by reacting it with phenol or the appropriate substituted phenol to give a silylated phenyl or substituted phenyl ester. Finally, the silyl groups are replaced by free hydroxy moieties by hydrolysis under acidic conditions. For this purpose dilute acetic acid may be advantageously used.

An alternative method for alkyl, cycloalkyl or aralkyl esterification of the carboxyl moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Various methods are available for preparing phenyl esters, substituted phenyl esters and particularly the following esters of this invention:

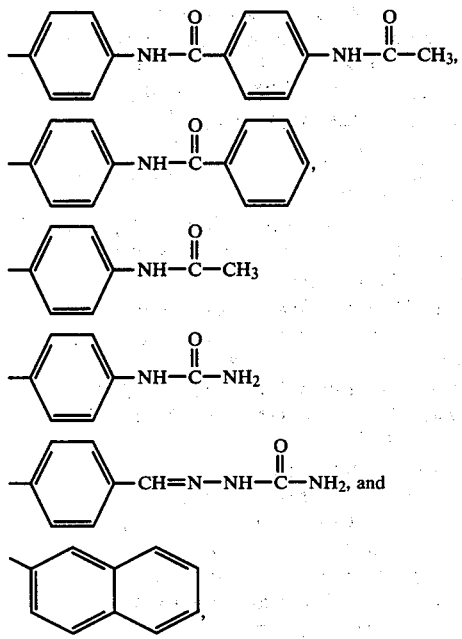

from corresponding phenols or naphthol and the free acid of a prostaglandin-type compound differing as to yield and purity of product.

Thus by one method, the PG compound is converted to a tertiary amine salt, reacted with pivaloyl halide to give the mixed acid anhydride and then reacted with the phenol. Alternatively, instead of pivaloyl halide, an alkyl or phenylsulfonyl halide is used, such as p-toluenesulfonyl chloride. See for example Belgiam Pat. Nos. 775,106 and 776,294, Derwent Farmdoc Nos. 33705T and 39011T.

Still another method is by the use of the coupling reagent, dicyclohexylcarbodiimide. See Fieser et al., "Reagents for Organic Synthesis", pp. 231-236, John Wiley and Sons, Inc., New York (1967). The PG compound is contacted with one to ten molar equivalents of the phenol in the presence of 2-10 molar equivalents of dicyclohexylcarbodiimide in pyridine as a solvent.

The preferred novel process for the preparation of these esters, however, comprises the steps (1) forming a mixed anhydride with the prostaglandin-type compound and isobutylchloroformate in the presence of a tertiary amine and (2) reacting the anhydride with an appropriate phenol or naphthol.

The mixed anhydride is represented by the formula:

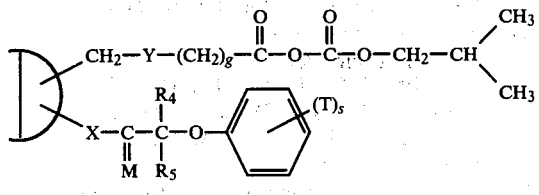

for the optically active PG compounds, D, $R_4$, $R_5$, M, T, s, X and Y, all having the same definition as hereinabove.

The anhydride is formed readily at temperatures in the range $-40°$ to $+60°$ C., preferably at $-10°$ to $+10°$ C. so that the rate is reasonably fast and yet side reactions are minimized. The isobutylchloroformate reagent is preferably used in excess, for example 1.2 molar equivalents up to 4.0 per mole of prostaglandin-type compound. The reaction is preferably done in a solvent and for this purpose acetone is preferred, although other relatively non-polar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The phenol is preferably used in equivalent amounts or in excess to insure that all of the mixed anhydride is converted to ester. Excess phenol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. Although they may be used, 2-methylpyridine and quinoline result in a slow reaction. A highly hindered amine such as 2,6-dimethyllutidine is not useful because of the slowness of the reaction.

The reaction with the anhydride proceeds smoothly at room temperature (about 20° to 30° C.) and can be followed in the conventional manner with thin layer chromatography.

The reaction mixture is worked up to yield the ester following methods known in the art, and the product is purified, for examply by silica gel chromatography.

Solid esters are converted to a free-flowing crystalline form on crystallization from a variety of solvents, including ethyl acetate, tetrahydrofuran, methanol, and acetone, by cooling or evaporating a saturated solution of the ester in the solvent or by adding a miscible non-solvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 75° C. Although the crystals are normally pure enough for many applications, they may be recrystallized by the same general techniques to achieve improved purity after each recrystallization.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

The acids or esters of this invention prepared by the processes of this invention are transformed to lower alkanoates by interaction of a free hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent.

Alternatively an inert organic diluent, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography or crystallization.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer on deuterochloroform solutions with tetramethylsilane as an internal standard (downfield).

Mass spectra are recorded on a CEG Model 110B Double Focusing High Resolution Mass Spectrometer or an LKB Model 9000 Gas-Chromatograph-Mass Spectrometer (ionization voltage 70 ev). Trimethylsilyl derivatives are used.

The collection of chromatographic eluate fractions starts when the eluant front reaches the bottom of the column in those cases employing a dry-packed column.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966). "Skellysolve-B" (SSB) refers to mixed isomeric hexanes.

Silica gel chromatography, as used herein, is understood to include elution, collection of fractions, and combination of those fractions shown by TLC (thin layer chromatography) to contain the desired product free of starting material and impurities.

Melting points (MP) are determined on a Fisher-Johns melting point apparatus.

DDQ refers to 2,3-dichloro-5,6-dicyano-1,4-benzoquinone.

Specific Rotations, [α], are determined for solutions of a compound in the specified solvent at ambient temperature with a Perkin-Elmer Model 141 Automatic Polarimeter.

Preparation 1
3α-Benzoyloxy-2β-carboxaldehyde-5α-hydroxy-1α-cyclopentaneacetic Acid γ-Lactone
(Formula XVII: $R_9$ is benzoyl).

Refer to Chart A.

A. To a mixture of formula-XIII laevorotatory (−) 3α-hydroxy-5α-hydroxy-4-iodo-2β-methoxy-methyl-1α-cyclopentaneacetic acid γ-lactone (E. J. Corey et al., J. Am. Chem. Soc. 92, 297 (1970), 75 g.) ir 135 ml. of dry pyridine under a nitrogen atmosphere is added 30.4 ml. of benzoyl choride with cooling to maintain the temperature at about 20°–40° C. Stirring is continued for an additional 30 min. About 250 ml. of toluene is added and the mixture concentrated under reduced pressure. The residue is dissolved in one liter of ethyl acetate, washed with 10% sulfuric acid, brine, aqueous saturated sodium bicarbonate, and brine. The ethyl acetate solution is dried over sodium sulfate and concentrated under reduced pressure to yield an oil, 95 g. Crystallization of the oil yields the corresponding 3α-benzoyloxy compound, m.p. 84°–86° C.; $[α]_D$ +7° (CHCl₃); infrared spectral absorptions at 1768, 1722, 1600, 1570, 1490, 1275, 1265, 1180, 1125, 1090, 1060, 1030, and 710 cm$^{-1}$; and NMR (nuclear magnetic resonance) peaks at 2.1–3.45, 3.3, 3.58, 4.38, 5.12, 5.51, 7.18–7.58, and 7.83–8.05 δ.

B. The iodo group is removed as follows. To a solution of the above benzoyloxy compound (60g.) in 240 ml. of dry benzene is added 2,2′-azobis-(2-methylpropionitrile) (approximately 60 mg.). The mixture is cooled to 15° C. and to it is added a solution of 75 g. tributyltin hydride in 600 ml. of ether, with stirring, at such a rate as to maintain continuous reaction at about 25° C. When the reaction is complete as shown by TLC (thin layer chromatography) the mixture is concentrated under reduced pressure to an oil. The oil is mixed with 600 ml. of Skellysolve B (mixed isomeric hexanes) and 600 ml. of water and stirred for 30 min. The water layer, containing the product, is separated, then combined with 450 ml. of ethyl acetate and enough solid sodium chloride to saturate the aqueous phase. The ethyl acetate layer, now containing the product, is separated, dried over magnesium sulfate, and concentrated under reduced pressure to an oil, 39 g. of the iodine-free compound. An analytical sample gives $[\alpha]_D$ −99° (CHCl$_3$); infrared spectral absorptions at 1775, 1715, 1600, 1585, 1490, 1315, 1275, 1180, 1110, 1070, 1055, 1025, and 715 cm$^{-1}$.; NMR peaks at 2.5–3.0, 3.25, 3.34, 4.84–5.17, 5.17–5.4, 7.1–7.5, and 7.8–8.05 δ; and mass spectral peaks at 290, 168, 105, and 77.

C. The 2β-methoxymethyl compound is changed to a hydroxymethyl compound as follows. To a cold (0.5° C.) solution of the above iodine-free methoxy-methyl lactone (20 g.) in 320 ml. of dichloromethane under nitrogen is added a solution of 24.8 ml. of boron tribromide in 320 ml. of dichloromethane, dropwise with vigorous stirring over a period of 50 min. at 0°–5° C. Stirring and cooling are continued for one hour. When the reaction is complete, as shown by TLC, there is cautiously added a solution of sodium carbonate (78 g.) monohydrate in 200 ml. of water. The mixture is stirred at 0°–5° C. for 10–15 min., saturated with sodium chloride, and the ethyl acetate layer separated. Additional ethyl acetate extractions of the water layer are combined with the main ethyl acetate solution. The combined solutions are rinsed with brine, dried over sodium sulfate and concentrated under reduced pressure to an oil, 18.1 g. of the 2β-hydroxymethyl compound. An analytical sample has m.p. 116°–118° C.; $[\alpha]_D$ −80° (CHCl$_3$); infrared spectral absorptions at 3460, 1735, 1708, 1600, 1580, 1490, 1325, 1315, 1280, 1205, 1115, 1090, 1070, 1035, 1025, 730, and 720; and NMR peaks at 2.1–3.0, 3.58, 4.83–5.12, 5.2–5.45, 7.15–7.55, and 7.8–8.0 δ.

D. The title 2β-carboxaldehyde compound is prepared as follows. To a mixture of 250 ml. of dichloromethane and Collins' reagent prepared from chromium trioxide (10.5 g.) and 16.5 ml. of pyridine, cooled to 0° C., a cold solution of the hydroxymethyl compound of step C (5.0 g.) in 50 ml. of dichloromethane is added, with stirring. After 7 min. of additional stirring, the title intermediate is used directly without isolation (see Example 1).

Following the procedure of Preparation 1, but replacing that optically active formula-XIII iodolactone with the racemic compound of that formula and the mirror image thereof (see E. J. Corey et al., J. Am. Chem. Soc. 91, 5675 (1969)) there is obtained the racemic compound corresponding to formula XVII.

Preparation 2

3α-Benzoyloxy-5α-hydroxy-2β-(3-oxo-4-phenoxy-trans-1-butenyl)-1α-cyclopentaneacetic Acid, γ-Lactone (Formula XVIII: R$_4$ and R$_5$ are hydrogen, R$_9$ is benzoyl, and s is zero).

Refer to Chart B.

A. There is first prepared dimethyl3-phenoxyacetonylphosphate. A solution of dimethyl methylphosphonate (75 g.) in 700 ml. of tetrahydrofuran is cooled to −75° C. under nitrogen and n-butyllithium (400 ml. of 1.6 molar solution in hexane) is added, keeping the temperature below −55° C. The mixture is stirred for 10 min. and to it is slowly added 2-phenoxyacetyl chloride (44 g.), again keeping the temperature below −55° C. The reaction mixture is stirred at −75° C. for 2 hours, then at about 25° C. for 16 hours. The mixture is acidified with acetic acid and concentrated under reduced pressure. The residue is partioned between diethyl ether and water, and the organic phase is dried and concentrated to the above-named intermediate, 82 g. Further treatment by silica gel chromatography yields an analytical sample having NMR peaks at 7.4–6.7 (multiplet), 4.78 (singlet), 4.8 and 4.6 (two singlets), and 3.4–3.04 (doublet) δ.

B. The phosphonate anion (ylid) is then prepared as follows. Dimethyl 3-phenoxyacetonylphosphonate (step A, 9.3 g.) is added in portions to a cold (5° C.) mixture of sodium hydride (1.75 g. of 50% in 250 ml. of tetrahydrofuran, and the resulting mixture is stirred for 1.5 hours at about 25° C.

C. To the mixture of step B is added the cold solution of the formula-XVII 2β-carboxaldehyde of Preparation 1, and the resulting mixture is stirred about 1.6 hours. Then 3 ml. of acetic acid is added and the mixture is concentrated under reduced pressure. A solution is prepared from the residue in 500 ml. of ethyl acetate, washed with several portions of water and brine, and concentrated under reduced pressure. The residue is subjected to silica gel chromatography, eluting with ethyl acetate-Skellysolve B (isomeric hexanes) 3:1). Those fractions shown by TLC to be free of starting material and impurities are combined and concentrated to yield the title compound, 1.7 g.; NMR peaks at 5.0–8.2 and 4.7 (singlet) δ.

Following the procedure of Preparation 2, but replacing the optically active formula-XVII aldehyde with the racemic aldehyde obtained after Preparation 1, there is obtained the racemic 3-oxo-4-phenoxy-1-butenyl compound corresponding to formula XVIII.

Following the procedure of Preparation 2, but replacing 2-phenoxyacetyl chloride with each of the following acid esters:

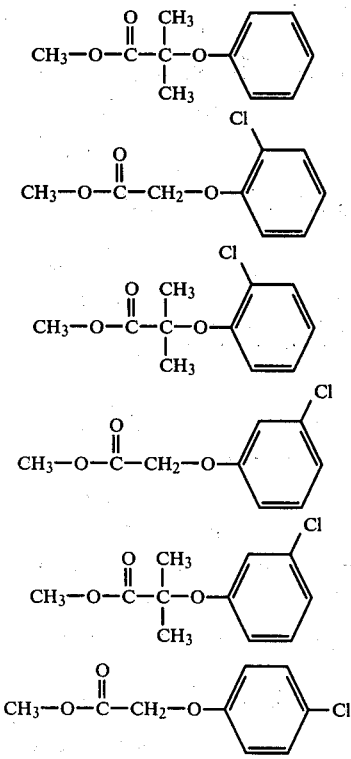

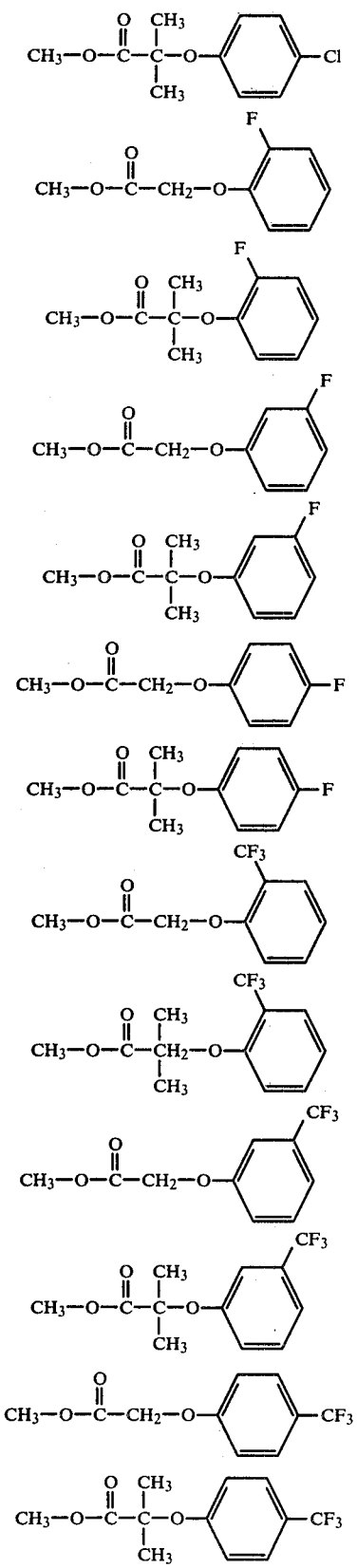
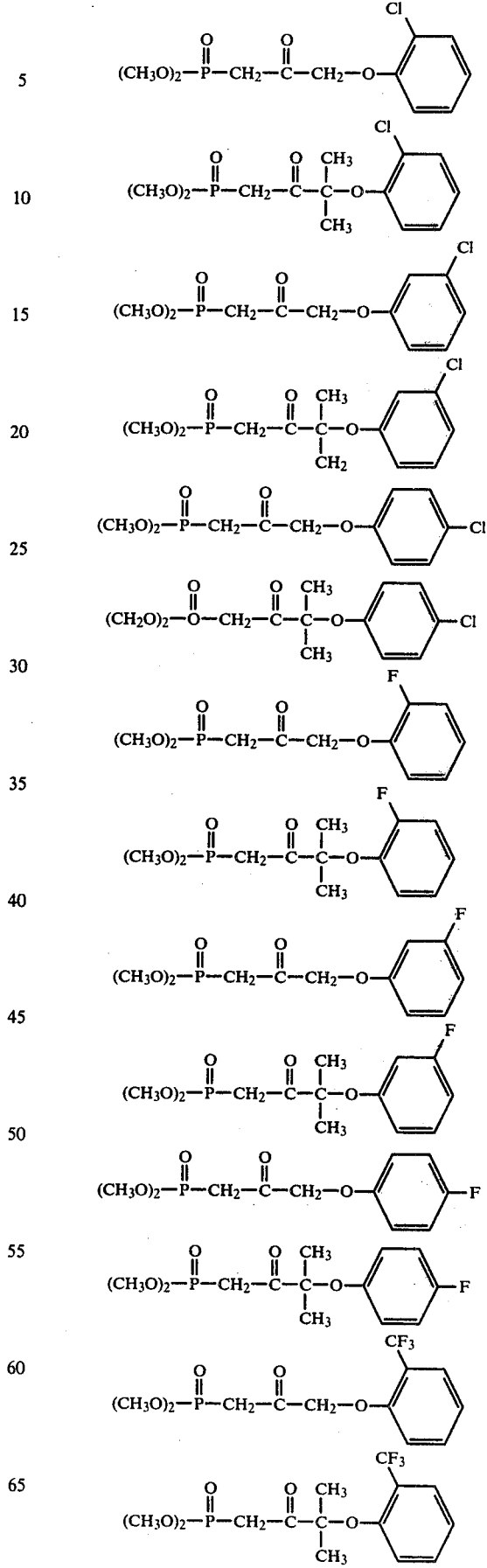
there is respectively obtained the corresponding phosphonate:
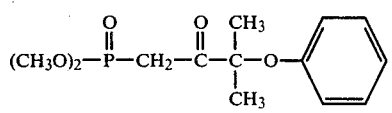

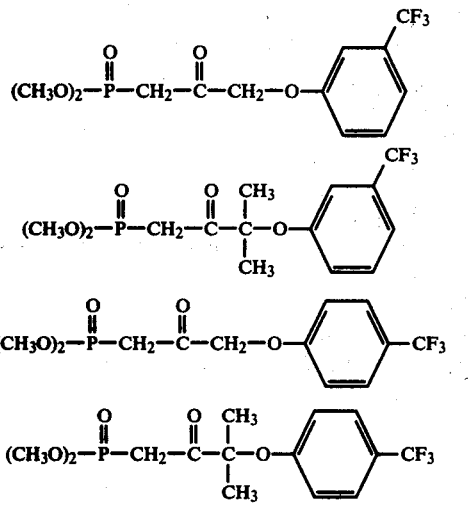

and thence the formula-XVIII lactone:

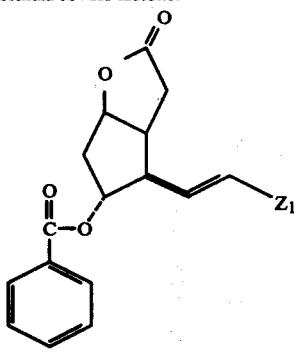

wherein $Z_1$ is respectively:

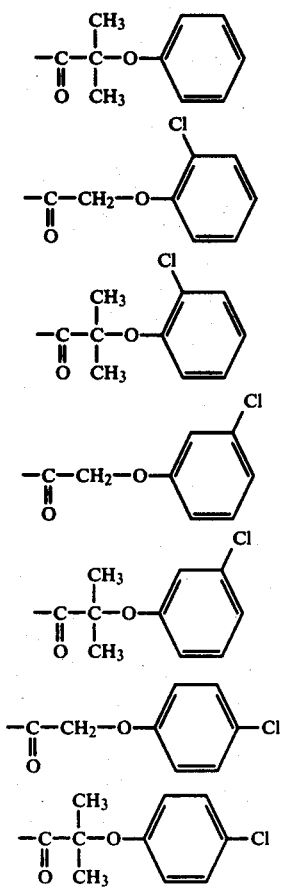

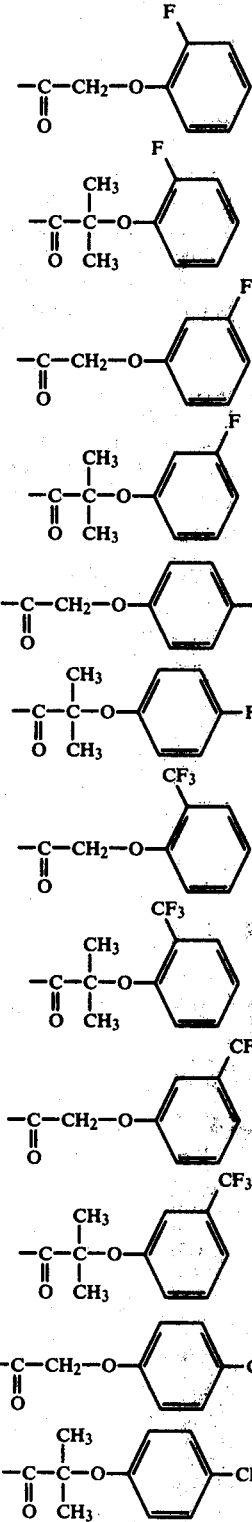

When a phosphonate contains an asymmetric carbon atom, e.g. when the methylene between the carbonyl and the —O— is substituted with only one methyl or ethyl group, the phosphonate exists in either of two optically active forms (+ or —) or their racemic (dl) mixture. An optically active phosphonate is obtained by starting with an appropriate optically active isomer of a phenoxy or substituted-phenoxy aliphatic acid. Methods of resolving these acids are known in the art, for example by forming salts with an optically active base such as brucine, separating the resulting diastereomers, and recovering the acids.

Following the procedure of Preparation 2, employing the optically active aldehyde XVII of that example, each optically active phosphonate yields a corresponding optically active formula-XVIII γ-lactone.

Likewise following the procedure of Preparation 2, employing the optically active aldehyde XVII of that preparation, each racemic phosphonate obtained yields a pair of diastereomers, differing in their stereochemistry at the fourth carbon of the phenoxy-terminated side-chain. These diastereomers are separated by conventional methods, e.g. by silica gel chromatography.

Again following the procedure of Preparation 2, employing the optically active aldehyde XVII of that example, each of the optically inactive phosphonates obtained from the list of carboxy acid esters above wherein there is no asymmetric carbon atom, i.e. $R_4$ and $R_5$ are the same, yields a corresponding optically active formula-XVIII γ-lactone.

Replacing the optically active aldehyde XVII with the racemic aldehyde obtained after Preparation 1, and following the procedure of Preparation 2 using each of the optically active phosphonates described above, there is obtained in each case a pair of diastereomers which are separated by chromatography.

Likewise following the procedure of Preparation 2, employing the racemic aldehyde with each of the racemic phosphonates described above, there are obtained in each case two pairs of 3-oxo-4-phenoxy (or substituted-phenoxy) racemates which are separated into pairs of racemic compounds by methods known in the art, e.g. silica gel chromatography.

Again following the procedure of Preparation 2, employing the racemic aldehyde with each of the optically active phosphonates described above, there are obtained in each case a diastereomeric product corresponding to formula XVIII.

Preparation 3
3α-Benzoyloxy-5α-hydroxy-2β-(3α-hydroxy-3-methyl-4-phenoxy-trans-1-butenyl-1α-cyclopentaneacetic Acid, γ-Lactone (Formula XXXI: $M_6$ is

and Q is

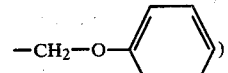

and the 3β-hydroxy epimer (Formula XXXI: $M_6$ is

and Q is

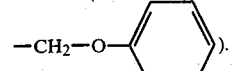

To a stirred solution of 1.0 g. of 3αs-benzoyloxy-5α-hydroxy-2β-(3-oxa-4-phenoxy-trans-1-butenyl)-1α-cyclopentaneacetic acid, γ-lactone in 75 ml. of tetrahydrofuran at −78° C. under nitrogen is added dropwise 15 ml. of an ethereal solution of 3M methyl magnesium bromide. The solution becomes heterogeneous. After two hours a TLC (50% ethyl acetate-Skellysolve B) of an aliquot quenched with ether-ammonium chloride shows the reaction to be complete. To the mixture at −78° C. is added dropwise 15 ml. of saturated aqueous ammonium chloride. The resulting mixture is allowed to warm with stirring to ambient temperatures. The mixture is then diluted with diethyl ether and water, equilibrated, and separated, the aqueous layer is extracted three times more with diethyl ether. The organic extracts are combined, washed with brine, dried over sodium sulfate, and evaporated to give the product.

Following the procedure of Preparation 3, but using each of the formula-XVIII lactones, described in the text following Preparation 2 above, there are obtained the lactones of the formula

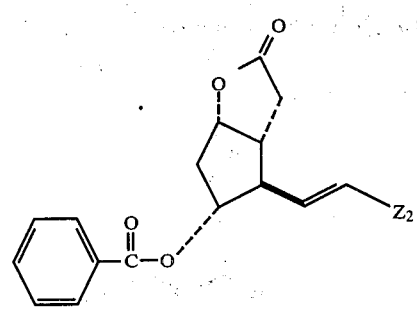

wherein $Z_2$ is respectively;

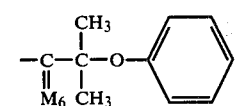

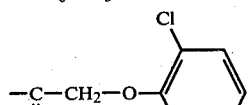

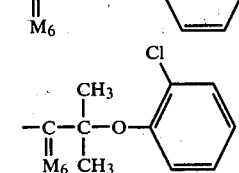

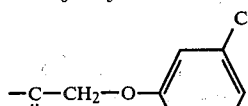

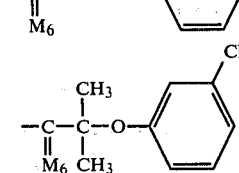

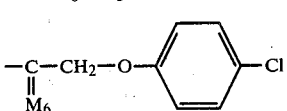

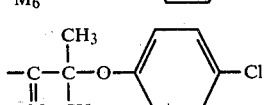

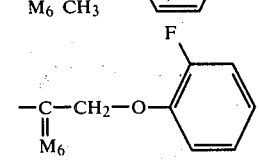

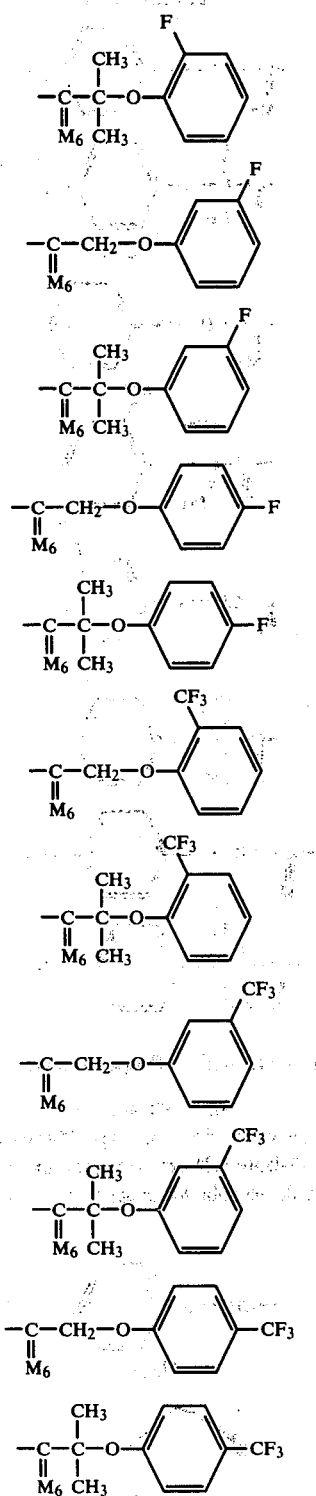

wherein M₆ is as defined in Preparation 3.

Following the procedure of Preparation 3, but using a racemic lactone described following Preparation 2, there are obtained corresponding racemic 3-methyl products.

Preparation 4
3α,5α-dihydroxy-2β-(3α-hydroxy-3-methyl-4-phenoxy-trans-1-butenyl)-1α-cyclopentaneacidaldehyde, γ-lactol bis(tetrahydropyranyl) ether (Formula XXXIV: wherein M₇ is

Q is

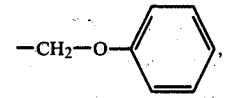

∼ is α or β, and R₁₀ is THP) and the 3β-hydroxy epimer, (Formula XXXIV: wherein M₇ is

and Q, ∼, and R₁₀ are as defined above herein).

A. With reference to Chart E the formula-XXXI compound (the compound of Preparation 3, 1.3 g.) in 22 ml. of anhydrous methanol is stirred with potassium carbonate (0.48 g.) for one hour at about 25° C. and 15 ml. of chloroform is added and the solvent removed under reduced pressure. A solution of the residue in 70 ml. of chloroform is shaken with 10 ml. of water containing potassium hydrogen sulfate (0.5 g.), then with the brine, and concentrated. The residue is washed with several portions of Skellysolve B (isomeric hexanes) and dried to yield the formula-XXXII compound, 3α,-5α-dihydroxy-2β(3α-hydroxy-3-methyl-4-phenoxy-trans-1-butenyl)-1α-cyclopentaneacetic acid, γ-lactone, and its 3-hydroxy epimer, 0.4 g.

B. The formula-XXXII compound from part A above is converted to the formula-XXXIII bis(tetrahydropyranyl) ether by reaction with 0.8 ml. of dihydropyran in 10 ml. of dichloromethane in the presence of pyridine hydrochloride (about 0.03 g.). In about 2.5 hours the mixture is filtered and concentrated to the formula-XXXIII product, 0.6 g.

C. The title compound is prepared as follows. Diisobutylaluminumhydride (4.8 ml. of a 10 percent solution in toluene) is added dropwise to a stirred solution of the above formula-XXXIII bis(tetrahydropyranyl) ether from part B above in 8 ml. of toluene cooled to −78° C. Stirring is continued at −78° C. for 0.5 hours whereupon a solution of 3 ml. of tetrahydrofuran and 1 ml. of water is added cautiously. After the mixture warms to 25° C. it is filtered and the filtrate is washed with brine, dried, and concentrated to the mixed alpha and beta hydroxy isomers of the formula-XXXIV title compound.

Following the procedure of Preparation 4, each of the optically active or racemic compounds corresponding to formula XXXI described the following Preparation 3 is transferred to an optically active or racemic compound corresponding to formula XXXIV. There are thus obtained both 3α- and 3β-hydroxy isomers.

Further, using the various phenoxy substituted and/or 16-alkyl substituted formula-XXXI intermediates provided herein following Preparation 3, there are prepared, following the procedures of Preparation 4, the following formula-XXXIV compounds:

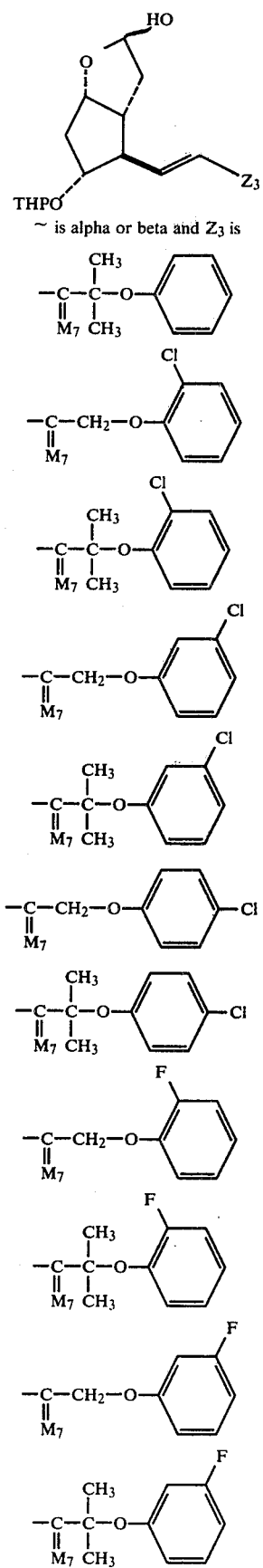

~ is alpha or beta and Z₃ is

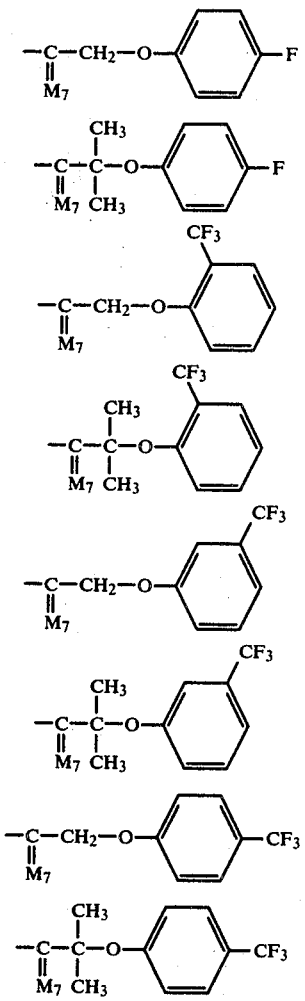

wherein $M_7$ is as defined in Preparation 4.

Preparation 5

3α-Benzoyloxy-5α-hydroxy-2β-(3α-hydroxy-4-phenoxy-trans-1-butenyl)-1α-cyclopentaneacetic Acid, γ-Lactone (Formula XIX: $R_9$ is benzoyl, Q is

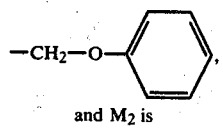

and $M_2$ is

or the 3β-hydroxy epimer (Formula XIX: $R_9$ is benzoyl, Q is

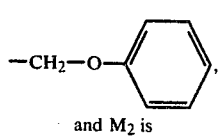

and $M_2$ is

Refer to Chart B. A solution containing ketone XVIII (Preparation 2, 2.7 g.) in 14 ml. of 1,2-dimethoxyethane is added to a mixture of zinc borohydride, prepared from zinc chloride (anhydrous, 4.9 g.) in sodium borohydride (1.1 g.) in 48 ml. of dry 1,2-dimethoxyethane, with stirring and cooling to $-10°$ C. Stirring is continued for 2 hours at $0°$ C., and water (7.8 ml.) is cautiously added, followed by 52 ml. of ethyl acetate. The mixture is filtered, and the filtrate is separated. The ethyl acetate solution is washed with brine, dried over sodium sulfate, and concentrated under reduced pressure to a mixture of the corresponding formula-XVIII alpha and beta isomers. The compounds are chromatographed on silica gel, eluting with ethyl acetate, to separate the alpha and beta isomers of the formula XIX compounds.

Following the procedures of Preparation 5, but using the substituted-phenoxy and/or 4-methyl substituted ketones of formula XVIII which are shown herein following Preparation 2, the following optically active lactones are obtained:

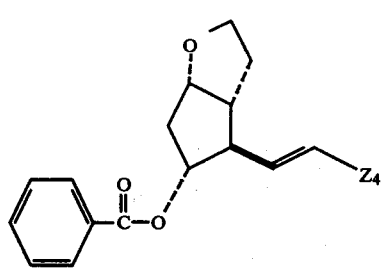

wherein $Z_4$ is respectively:

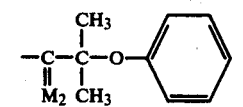

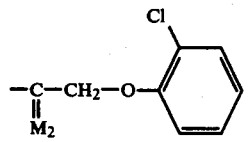

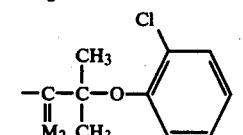

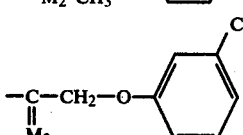

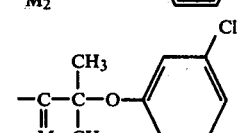

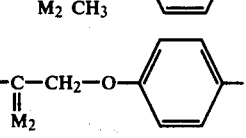

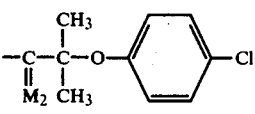

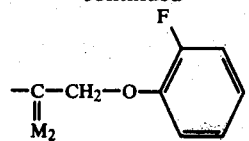

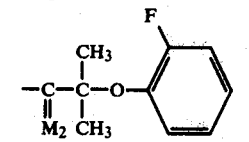

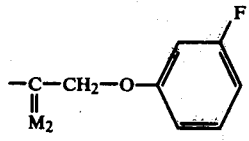

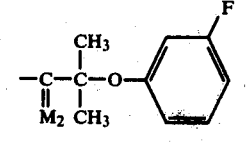

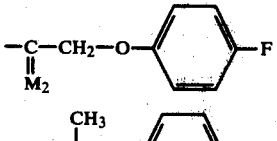

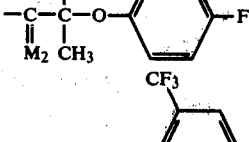

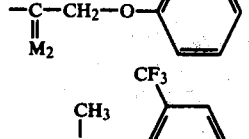

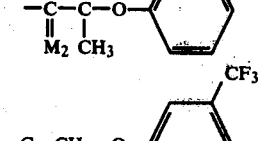

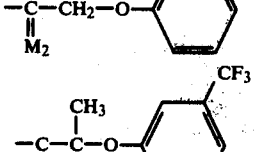

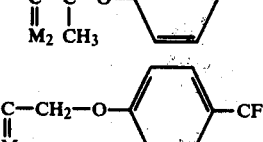

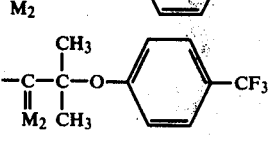

wherein $M_2$ is

or

Preparation 6
3α-Benzoyloxy-5α-hydroxy-2β-(3α-methoxy-4-phenoxy-trans-1-butenyl)-1α-cyclopentaneacetic Acid γ-Lactone (Formula XXVIII: $M_5$ is

and $R_9$ is benzoyl) or its 3β-methoxy epimer (Formula XXVIII: $M_5$ is

and $R_9$ is benzoyl).

Refer to Chart D where formulas for compounds XIX through XXX are shown. A mixture of the formula-XIX alpha hydroxy compound (Preparation 5, 2.0 g.), silver oxide (4.0 g.), and 50 ml. of methyl iodide is stirred and heated at reflux for 68 hours. The mixture is cooled and filtered, and the filtrate concentrated to an oil, 2.0 g. Separation by silica gel chromatography, eluting with 35% ethyl acetate Skellysolve B and combining those fractions shown by TLC to contain the product free of starting material and impurities, yields the formula XXVIII title compound as an oil.

Following the procedures of Preparation 6 and using each of the optically active or racemic formula-XIX hydroxy compounds following Preparation 5, is transformed to the corresponding optically active formula XXVIII methyl ether compound or racemate consisting of that compound and its mirror image.

Preparation 7
3α,5α-Dihydroxy-2β-(3α-methoxy-4-phenoxy-trans-1-butenyl)-(1α-cyclopentaneacetaldehyde, λ-lactol, tetrahydropyranyl ether (Formula XXIX: $M_5$ is

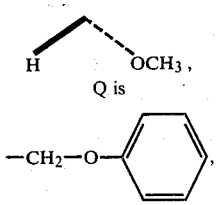

~ is alpha or beta, and $R_{10}$ is THP).
Refer to Chart D.

A. The formula-XXVIII benzoyloxy compound (1.9 g.) and anhydrous potassium carbonate (0.68 g.) in 25 ml. of dry methanol is stirred for one hour with extraction of moisture. Chloroform (25 ml.) is added and the mixture is filtered. The filtrate is concentrated to an oil which is taken up in chloroform (50 ml.). The solution is washed with brine, dried over magnesium sulfate, and concentrated to an oil. Separation by silica gel chromatography, eluting with 40 percent ethyl acetate-SSB and combining these fractions shown by TLC to contain the product free from starting material impurities, yields the deacylated compound.

B. The tetrahydropyranyl (THP) ether is prepared as follows

A mixture of the compound from part A above (2.35 g.), dihydropyran (3.5 g.), and p-toluenesulfonic acid (about 0.01 g.) in 150 ml. of dichloromethane is stirred for 30 minutes. The mixture is washed twice with sodium carbonate (10 percent) solution, and brine, and dried over magnesium sulfate. Concentration under reduced pressure yields the THP ether.

C. The formula-XXIX lactol is prepared as follows

To the solution of the above THP ether in 150 ml. of dry toluene is added with stirring, protected from air with nitrogen, a solution of 105 ml. of diisobutylaluminumhydride (10 percent in toluene) for about 35 min. at about −65° C. Stirring is continued for 30 min., with cooling. The cooling bath is removed, and the mixture of 48 ml. of tetrahydrofuran (THF) and 29 ml. of water is added dropwise over 20 min. The mixture is filtered and the filtrate is washed with brine and dried over magnesium sulfate. Concentration under reduced pressure yields the title compound as an oil.

Following the procedure of Preparations 5, 6, and 7, but using as starting materials the compounds described in the text following preparation 5 there are prepared the 3α- or 3β-methoxy lactols:

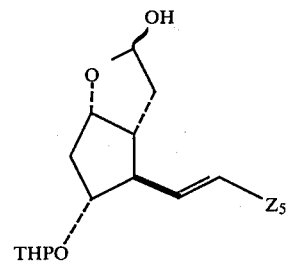

wherein $Z_5$ is respectively:

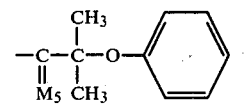

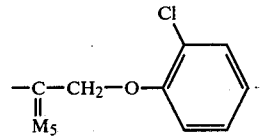

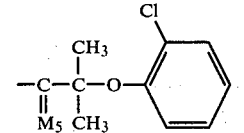

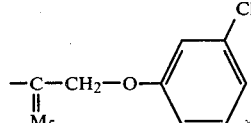

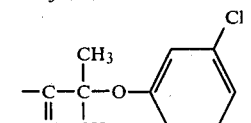

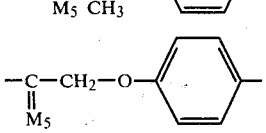

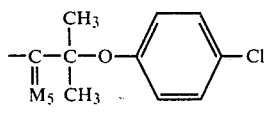

61
-continued

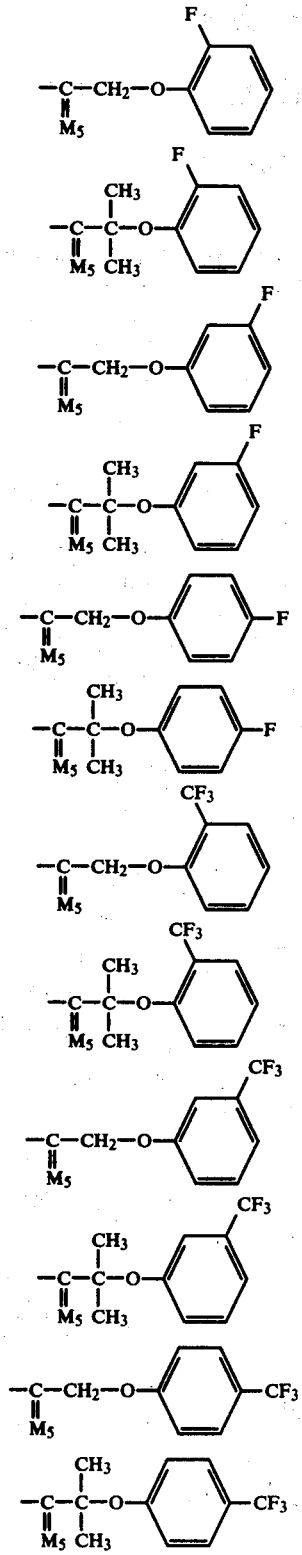

wherein M5 is

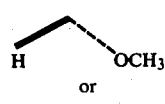
or

Preparation 8
(6-carboxyhexyl)triphenylphosphonium bromide.

A mixture of 63.6 g. of 7-bromoheptanoic acid in 80 g. of triphenylphosphine, and 300 ml. of acetonitrile is refluxed for 68 hours. Then 200 ml. of acetonitrile is removed by distillation. After the remaining solution has cooled to room temperature, 300 ml. of benzene is added with stirring. After adding a seed crystal, the mixture is allowed to stand overnight. The solid which separated is collected by filtration giving 134.1 g. of the product as white prisms, melting point 185°-187°. A portion is recrystallized from methanol-ether affording white prisms, melting point 185°-187°. The infrared spectrum shows absorptions at 2850, 2570, 2480, 1710, 1585, 1485, 1235, 1200, 1185, 1160, 1115, 1000, 755, 725, and 695 cm.$^{-1}$ NMR peaks are observed at 1.2-1.9, 2.1-2.6, 3.3-4.0, and 7.7-8.0 $\delta$.

Preparation 9    p-Benzamidophenol

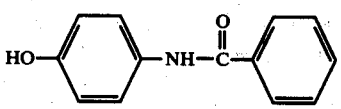

A solution of p-hydroxyaniline (20 g.) in 200 ml. of pyridine is treated with benzoic anhydride (20 g.). After 4 hours at about 25° C., the mixture is concentrated under reduced pressure and the residue is taken up in 200 ml. of hot methanol and reprecipitated with 300 ml. of water. The product is recrystallized from hot acetonitrile as white crystals, 8.5 g., melting point 218.0°-218.5° C.

Preparation 10
p-(p-Acetamidobenzamido)phenol

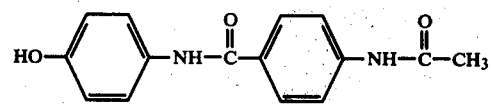

A solution of p-acetamidobenzoic acid (12.5 g.) in 250 ml. of tetrahydrofuran is treated with triethylamine (11.1 ml.). The mixture is then treated with isobutylchloroformate (10.4 ml.) and, after 5 min. at about 25° C., with p-aminophenol (13.3 g.) in 80 ml. of dry pyridine. After 40 min. the crude product is obtained by addition of 2 liters of water. The product is recrystallized from 500 ml. of hot methanol by dilution with 300 ml. of water as white crystals, 5.9 g., melting point 275.0°-277.0° C.

Example 1
15-Methyl-16-phenoxy-17,18,19,20-tetranor-PGF$_{2\alpha}$, Methyl Ester (Formula I: wherein ~ is alpha, g is 3, R$_1$ is methyl, M$_3$ is

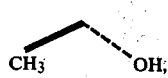

R$_4$ and R$_5$ are hydrogen, and s is 0).

Refer to Chart E.

A. (4-carboxybutyl)triphenylphosphonium bromide (E. J. Corey et al., J. Am. Chem. Soc. 94, 5677 (1969)) (4.43 g.) is added to a solution of sodio dimethylsulfinyl-carbanide prepared from sodium hydride (57 percent, 0.84 g.) and 14 ml. of dimethylsulfoxide (DMSO). To this reagent is added dropwise a solution of the formula-XXXIV lactol of Preparation 4 in 6 ml. of DMSO. The mixture is stirred at about 25° C. for 2 hours, then diluted with 80 ml. of benzene. To the mixture is added, with stirring, a solution of potassium hydrogen sulfate (4.1 g.) in 20 ml. of water. The organic layer is separated, washed with water, dried, and concentrated under reduced pressure. The residue is triturated with diethyl ether and cooled to 10° C. The liquid residue after evaporation is chromatographed on silica gel eluting with chloroform-methanol (10:1) and combining those fractions showed by TLC to contain the product free of starting material and impurities.

B. A solution of the bis(tetrahydropyranyl)ether of part A above (0.37 g.) in 1.5 ml. of acetonitrile is mixed with 15 ml. of 66 percent acetic acid. The mixture is heated to about 46° C. for 1.5 hours and then concentrated under reduced pressure. The residue is taken up in toluene and again concentrated. The residue is chromatographed on silica gel eluting with ethyl acetate-acetone-water (8:5:1). Those fractions shown by TLC to contain the deetherified product free from starting material and impurities are combined and concentrated to yield a mixture of the title compound and its 15-epimer.

C. A solution of diazomethane (about 0.5 g.) in 25 ml. of diethyl ether is added to a solution of the product of Part B above in 25 ml. of a mixture of methanol and diethylether (1:1). After the mixture stands at about 25° C. for 5 minutes, it is concentrated under reduced pressure to yield the methyl ester of the compound of Part B above. The 15α-epimer, the title compound of this example, is then separated from the 15β-epimer using high pressure liquid chromatography (HPLC).

Example 2
15-epi-15-Methyl-16-phenoxy-17,18,19,20-tetranor-PGF$_{2\alpha}$, Methyl Ester: (Formula I: wherein ~ is alpha, g is 3, $R_1$ is methyl, $M_3$ is

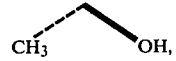

$R_4$ and $R_5$ are hydrogen, and s is 0).

Following the procedure of Example 1, the title compound of this example is obtained as from the HPLC chromatographic separation performed in part C of Example 1.

Example 3
15-Methyl-16-phenoxy-17,18,19,20-tetranor-PGF$_{2\alpha}$ (Formula I: wherein ~ is alpha, g is 3, $R_1$ is hydrogen, $M_3$ is

$R_4$ and $R_5$ are hydrogen, and s is 0).

Aqueous potassium hydroxide solution (45 percent, 0.9 ml.) is added to a solution of the compound of Example 1 (288 mg.) in a mixture of 6.8 ml. of methanol and 2.2 ml. of water under nitrogen. The resulting solution is stirred 2 hours at 25° C. and is then poured into several volumes of water. The aqueous mixture is extracted with ethyl acetate, acidified with 3M hydrochloric acid, saturated with sodium chloride, and then extracted repeatedly with ethyl acetate. The latter ethyl acetate extracts are combined, washed successively with water and saturated aqueous sodium chloride solution, dried with anhydrous sodium sulfate, and evaporated under reduced pressure. The residue so obtained comprises the title compound of this example in essentially pure form.

Example 4
15-epi-15-Methyl-16-phenoxy-17,18,19,20-tetranor-PGF$_{2\alpha}$ (Formula I: wherein ~ is alpha, g is 3, $R_1$ is H, $M_3$ is

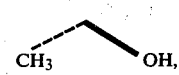

$R_4$ and $R_5$ are hydrogen, and s is 0).

Following the procedure of Example 3, using as starting material the compound of Example 1, the title compound of this example is prepared.

Using the procedure of Examples 1 and 3, the following 15-methyl-PGF$_{2\alpha}$-type compounds and their corresponding methyl esters are prepared from the lactol starting material of the formula:

| Example | $Z_3$ | 15-Methyl-PGF$_{2\alpha}$, Methyl Ester |
|---|---|---|
| 5 | -C(=M$_7$)(CH$_3$)-C(CH$_3$)-O-C$_6$H$_5$ | 16-methyl-16-phenoxy-18,19,20-trinor |
| 6 | -C(=M$_7$)-CH$_2$-O-C$_6$H$_4$-Cl (ortho) | 16-(o-chlorophenoxy)-17,18,19,20-tetranor |
| 7 | -C(=M$_7$)(CH$_3$)-C(CH$_3$)-O-C$_6$H$_4$-Cl (ortho) | 16-methyl-16-(o-chlorophenoxy)-18,19,20-trinor |
| 8 | -C(=M$_7$)-CH$_2$-O-C$_6$H$_4$-Cl (meta) | 16-(m-chlorophenoxy)-17,18,19,20-tetranor |
| 9 | -C(=M$_7$)(CH$_3$)-C(CH$_3$)-O-C$_6$H$_4$-Cl (meta) | 16-methyl-16-(m-chlorophenoxy)-18,19,20-trinor |
| 10 | -C(=M$_7$)-CH$_2$-O-C$_6$H$_4$-Cl (para) | 16-(p-chlorophenoxy)17,18,19,20-tetranor |

| Example | Z₃ | 15-Methyl-PGF$_{2\alpha}$, Methyl Ester |
|---|---|---|
| 11 | –C(M₇)(=)–C(CH₃)(CH₃)–O–C₆H₄–Cl | 16-methyl-16-(p-chlorophenoxy-18,19,20-trinor |
| 12 | –C(M₇)(=)–CH₂–O–C₆H₄–F (o) | 16-(o-fluorophenoxy)-17,18,19,20-tetranor |
| 13 | –C(M₇)(=)–C(CH₃)–O–C₆H₄–F (o) | 16-methyl-16-(o-fluorophenoxy-18,19,20-trinor |
| 14 | –C(M₇)(=)–CH₂–O–C₆H₄–F (m) | 16-(m-fluorophenoxy)-17,18,19,20-tetranor |
| 15 | –C(M₇)(=)–C(CH₃)–O–C₆H₄–F (m) | 16-methyl-16-(m-fluorophenoxy-18,19,20-trinor |
| 16 | –C(M₇)(=)–CH₂–O–C₆H₄–F (p) | 16-(p-fluorophenoxy)-17,18,19,20-tetranor-PGF$_{2\alpha}$ |
| 17 | –C(M₇)(=)–C(CH₃)–O–C₆H₄–F (p) | 16-methyl-16-(p-fluorophenoxy-18,19,10-trinor PGF$_{2\alpha}$ |
| 18 | –C(M₇)(=)–CH₂–O–C₆H₄–CF₃ (o) | 16-(o-trifluoromethylphenoxy)-17,18,19,20-trinor-PGF$_{2\alpha}$ |
| 19 | –C(M₇)(=)–C(CH₃)–O–C₆H₄–CF₃ (o) | 16-methyl-16-(o-trifluoromethylphenoxy)-18,19,20-trinor-PGF$_{2\alpha}$ |
| 20 | –C(M₇)(=)–CH₂–O–C₆H₄–CF₃ (m) | 16-(m-trifluoromethylphenoxy)-17,18,19,20-tetranor-PGF$_{2\alpha}$ |
| 21 | –C(M₇)(=)–C(CH₃)–O–C₆H₄–CF₃ (m) | 16-methyl-16-(m-trifluoromethylphenoxy)-18,19,20-trinor-PGF$_{2\alpha}$ |
| 22 | –C(M₇)(=)–CH₂–O–C₆H₄–CF₃ (p) | 16-(p-trifluoromethylphenoxy)-17,18,19,20-tetranor-PGF$_{2\alpha}$ |
| 23 | –C(M₇)(=)–C(CH₃)–O–C₆H₄–CF₃ (p) | 16-methyl-16-(p-trifluoromethylphenoxy)-18,19,20-trinor-PGF$_{2\alpha}$ | wherein M₇ is –C(CH₃)(H)–OTHP

Following the procedures of Examples 2 and 4, 15-epi-15-methyl-PGF$_{2\alpha}$-type free acids and methyl esters are prepared using as intermediates the lactols used for the preparation of Examples 5–23. Accordingly, for each and every one of the 15α-hydroxy compounds of Examples 5–23 there are prepared corresponding 15-epi compounds, comprising Examples 24–42.

Example 43

2a,2b-Dihomo-15-methyl-16-phenoxy-17,18,19,20-tetranor-PGF$_{2\alpha}$, Methyl Ester (Formula I: wherein ~ is alpha, g is 5, R₁ is methyl, M is $$\text{CH}_3 \quad \text{OH},$$

R₄ and R₅ are hydrogen, and s is 0).

Following the procedure of Example 1, but using (6-carboxyhexyl)triphenylphosphonium bromide (Preparation 8) in place of (4-carboxybutyl)triphenylphosphonium bromide the title compound of this example is prepared.

Example 44

2a,2b-Dihomo-15-methyl-16-phenoxy-17,18,19,20-tetranor-PGF$_{2\alpha}$ (Formula I: wherein ~ is alpha, g is 5, R₁ is hydrogen, M is $$\text{CH}_3 \quad \text{OH},$$

R₄ and R₅ are hydrogen, and s is 0).

Following the procedure of Example 3, but using the compound of Example 43 in place of the compound of Example 1, the title compound of this example is prepared.

The 15-epimers of the compounds of Examples 43 and 44, that is the free acid or methyl ester of 2a,2b-dihomo-15-epi-15-methyl-16-phenoxy-17,18,19,20-tetranor-PGF$_{2\alpha}$, are prepared by the procedures of Examples 2 and 4 from the same lactol starting materials of Examples 2 and 4 but using the (6-carboxyhexyl)triphenylphosphonium bromide. These 15(R)-epimers thus are the compounds of Examples 45 and 46.

There are prepared further 2a,2b-dihomo-PGF$_{2\alpha}$-type compounds using the lactol starting material of Examples 5 through 23, respectively. Reaction in turn of each of these lactols with (6-carboxyhexyl)triphenylphosphonium bromide yields a corresponding 2a,2b-dihomo-15-methyl-PGF$_{2\alpha}$-type compound. Accordingly, each of the lactols of Examples 5-23 yield in free acid or methyl ester form a corresponding 2a,2b-dihomo-PGF$_{2\alpha}$-type product. These compounds thus provide Examples 47-65.

Following the procedure for Examples 45 and 46, but using the lactol starting material of Examples 47-65, there are prepared 15-epimers of each of the PGF$_{2\alpha}$-type compounds of Examples 47-65, above. Accordingly, there are provided 2a,2b-dihomo-15-epi-15-methyl-PGF$_{2\alpha}$-type compounds in either the free acid or methyl ester form comprising Examples 66-84.

Example 85
16-Phenoxy-17,18,19,20-tetranor-PGF$_{2\alpha}$, 15-Methyl Ether, Methyl Ester (Formula I: wherein ~ is alpha, g is 3, R$_1$ is methyl, M$_3$ is

R$_4$ and R$_5$ are hydrogen, and s is zero).

Following the procedure of Example 1, but using the 3α-methoxy lactol of Preparation 7 in place of the compound of Preparation 4, and omitting the final chromatographic separation carried out in Example 1, title compound of this example is prepared.

Following the procedure described in Example 85, but omitting the esterification with diazomethane, the free acid form of the compound of Example 85 is prepared. Accordingly, 16-phenoxy-17,18,19,20-tetranor-PGF$_{2\alpha}$, 15-methyl ether is provided as Example 86.

Following the procedure of Examples 85 and 86 but using as starting material the 3α-methoxy lactol of Preparation 7 there is prepared in both the free acid and methyl esterform 15-epi-16-phenoxy-17,18,19,20-tetranor-PGF$_{2\alpha}$, 15-methyl ether. These compounds accordingly provide Examples 87 and 88.

Following the procedures of Examples 85 and 86 there are obtained in either free acid or methyl ester form the following PGF$_{2\alpha}$, 15-methyl ether-type compounds using as starting material the 3α-methoxy lactols of Preparation 7 of the formula:

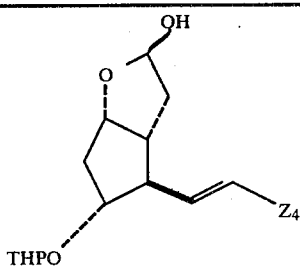

as follows:

| Ex. | Z$_4$ | PGF$_{2\alpha}$, Methyl Ether |
|---|---|---|
| 89 | -C(H)(OCH$_3$)-C(CH$_3$)$_2$-O-Ph | 16-methyl-16-phenoxy-18,19,20-trinor |

-continued

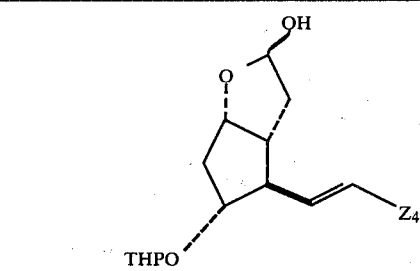

as follows:

| Ex. | Z$_4$ | PGF$_{2\alpha}$, Methyl Ether |
|---|---|---|
| 90 | -C(H)(OCH$_3$)-CH$_2$-O-(o-Cl-C$_6$H$_4$) | 16-(o-chlorophenoxy)-17,18,19,20-tetranor |
| 91 | -C(H)(OCH$_3$)-C(CH$_3$)$_2$-O-(o-Cl-C$_6$H$_4$) | 16-methyl-16-(o-chlorophenoxy-18,19,20-trinor |
| 92 | -C(H)(OCH$_3$)-CH$_2$-O-(m-Cl-C$_6$H$_4$) | 16-(m-chlorophenoxy)-17,18,19,20-tetranor |
| 93 | -C(H)(OCH$_3$)-C(CH$_3$)$_2$-O-(m-Cl-C$_6$H$_4$) | 16-methyl-16-(m-chlorophenoxy-18,19,20-trinor |
| 94 | -C(H)(OCH$_3$)-CH$_2$-O-(p-Cl-C$_6$H$_4$) | 16-(p-chlorophenoxy)-17,18,19,20-tetranor |
| 95 | -C(H)(OCH$_3$)-C(CH$_3$)$_2$-O-(p-Cl-C$_6$H$_4$) | 16-methyl-16-(p-chlorophenoxy-18,19,20-trinor |
| 96 | -C(H)(OCH$_3$)-CH$_2$-O-(o-F-C$_6$H$_4$) | 16-(o-fluorophenoxy)-17,18,19,20-tetranor |
| 97 | -C(H)(OCH$_3$)-C(CH$_3$)$_2$-O-(o-F-C$_6$H$_4$) | 16-methyl-16-(o-fluorophenoxy)-18,19,20-trinor |
| 98 | -C(H)(OCH$_3$)-CH$_2$-O-(m-F-C$_6$H$_4$) | 16-(m-fluorophenoxy)-17,18,19,20-tetranor |
| 99 | -C(H)(OCH$_3$)-C(CH$_3$)$_2$-O-(m-F-C$_6$H$_4$) | 16-methyl-16-(m-fluorophenoxy-18,19,20-trinor |
| 100 | -C(H)(OCH$_3$)-CH$_2$-O-(p-F-C$_6$H$_4$) | 16-(p-fluorophenoxy)-17,18,19,20-tetranor |
| 101 | -C(H)(OCH$_3$)-C(CH$_3$)$_2$-O-(p-F-C$_6$H$_4$) | 16-methyl-16-(p-fluorophenoxy-18,19,20-trinor | as follows:

| Ex. | Z₄ | PGF$_{2\alpha}$, Methyl Ether |
|---|---|---|
| 102 | —C(H)(OCH₃)—CH₂—O—C₆H₄(o-CF₃) | 16-(o-trifluoromethylphenoxy)-18,19,20-tetranor |
| 103 | —C(H)(OCH₃)—C(CH₃)₂—O—C₆H₄(o-CF₃) | 16-methyl-16-(o-trifluoromethyl-phenoxy)-18,19,20-trinor |
| 104 | —C(H)(OCH₃)—CH₂—O—C₆H₄(m-CF₃) | 16-(m-trifluoromethylphenoxy)-17,18,19,20-tetranor |
| 105 | —C(H)(OCH₃)—C(CH₃)₂—O—C₆H₄(m-CF₃) | 16-methyl-16-(m-trifluoromethylphenoxy)-18,19,20-trinor |
| 106 | —C(H)(OCH₃)—CH₂—O—C₆H₄(p-CF₃) | 16-(p-trifluoromethyl-phenoxy)-17,18,19,20-tetranor |
| 107 | —C(H)(OCH₃)—C(CH₃)₂—O—C₆H₄(p-CF₃) | 16-methyl-16-(p-trifluoromethyl-phenoxy)-18,19,20-trinor |

Following the procedures of Examples 87 and 88 the 15-epi-PGF$_{2\alpha}$, 15-methyl ether-type compounds are prepared using as lactol starting material the various lactols used in Examples 89–107, respectively. There are accordingly provided 19 15-epi-PGF$_{2\alpha}$, 15-methyl ethers comprising Examples 108–126.

Following the procedures provided in Examples 85–89 there are prepared in both free acid and methyl ester form 2a,2b-dihomo-PGF$_{2\alpha}$, 15-methyl ether compounds in both the 15α and 15β epimeric configurations by using (6-carboxyhexyl)triphenylphosphonium bromide in place of (4-carboxybutyl)triphenylphosphonium bromide. Accordingly, there are provided 40 free acid or methyl ester compounds comprising examples 127–166 from a lactol of the formula

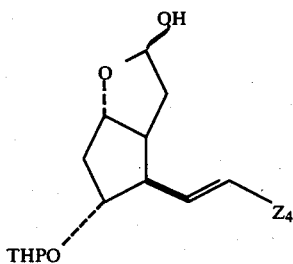

wherein ~ is alpha or beta, as follows:

| Ex. | Z₄ | M | 2a,2b-Diboro PGF$_{2\alpha}$, 15-Methyl Ether |
|---|---|---|---|
| 127 | —C(M₅)(=)—CH₂—O—C₆H₅ | H, OCH₃ | 16-phenoxy-17,18,19,20-tetranor |
| 128 | —C(M₅)(=)—CH₂—O—C₆H₅ | H, OCH₃ (epi) | 15-epi-16-phenoxy-17,18,19,20-tetranor |
| 129 | —C(M₅)(=)—C(CH₃)₂—O—C₆H₅ | H, OCH₃ | 16-methyl-16-20-phenoxy-18,19,trinor |
| 130 | —C(M₅)(=)—C(CH₃)₂—O—C₆H₅ | H, OCH₃ (epi) | 15-epi-16-methyl-16-phenoxy-18,19,20-trinor |
| 131 | —C(M₅)(=)—CH₂—O—C₆H₄(o-Cl) | H, OCH₃ | 16-(o-chlorophenoxy)-17,18-19,20-tetranor |
| 132 | —C(M₅)(=)—CH₂—O—C₆H₄(o-Cl) | H, OCH₃ (epi) | 15-epi-16(o-chlorophenoxy)-17,18,19,20-tetranor |
| 133 | —C(M₅)(=)—C(CH₃)₂—O—C₆H₄(o-Cl) | H, OCH₃ | 16-methyl-16-(o-chlorophenoxy)-18,19,20-trinor |
| 134 | —C(M₅)(=)—C(CH₃)₂—O—C₆H₄(o-Cl) | H, OCH₃ (epi) | 15-epi-16-methyl-16-(o-chlorophenoxy)-18,19,20-trinor |
| 135 | —C(M₅)(=)—CH₂—O—C₆H₄(m-Cl) | H, OCH₃ | 16-(m-chlorophenoxy)-17,18,-19,20-tetranor |
| 136 | —C(M₅)(=)—CH₂—O—C₆H₄(m-Cl) | H, OCH₃ (epi) | 15-epi-16-(m-chlorophenoxy)-17,18,19,20-tetranor |
| 137 | —C(M₅)(=)—C(CH₃)₂—O—C₆H₄(m-Cl) | H, OCH₃ | 16-methyl-16-(m-chlorophenoxy)-18,19,20-trinor |
| 138 | —C(M₅)(=)—C(CH₃)₂—O—C₆H₄(m-Cl) | H, OCH₃ (epi) | 15-epi-16-methyl-16(o-chlorophenoxy)-18,19,20-trinor |
| 139 | —CH₂—(M₅)—O—C₆H₄(p-Cl) | H, OCH₃ | 16-(p-chlorophenoxy)-17,18,19,20-tetranor |
| 140 | —C(M₅)(=)—CH₂—O—C₆H₄(p-Cl) | H, OCH₃ (epi) | 15-epi-16-(p-chlorophenoxy)-17,18,19,20-tetranor |
| 141 | —C(M₅)(=)—C(CH₃)₂—O—C₆H₄(p-Cl) | H, OCH₃ | 16-methyl-16-(p-chlorophenoxy)-18,19,20-trinor |
| 142 | —C(M₅)(=)—C(CH₃)₂—O—C₆H₄(p-Cl) | H, OCH₃ (epi) | 15-epi-16-methyl-16-(p-chlorophenoxy)-18,19,20-trinor |

| Ex. | Z₄ | M | 2a,2b-Diboro PGF$_{2\alpha}$, 15-Methyl Ether |
|---|---|---|---|
| 143 | $-\underset{\underset{M_5}{\parallel}}{C}-CH_2-O-\text{(o-F-C}_6H_4)$ | H OCH₃ | 16-(o-fluorophenoxy)-17,18,-19,20-tetranor |
| 144 | $-\underset{\underset{M_5}{\parallel}}{C}-CH_2-O-\text{(o-F-C}_6H_4)$ | H OCH₃ | 15-epi-16-(o-fluorophenoxy)-17,18,19,20-tetranor |
| 145 | $-\underset{\underset{M_5}{\parallel}}{\underset{\mid}{C}}-\underset{\underset{CH_3}{\mid}}{\overset{CH_3}{C}}-O-\text{(o-F-C}_6H_4)$ | H OCH₃ | 16-methyl-16-(o-fluorophenoxy)-18,19,20-trinor |
| 146 | $-\underset{\underset{M_5}{\parallel}}{\underset{\mid}{C}}-\underset{\underset{CH_3}{\mid}}{\overset{CH_3}{C}}-O-\text{(o-F-C}_6H_4)$ | H OCH₃ | 15-epi-16-methyl-16-(o-fluorophenoxy)-18,19,20-trinor |
| 147 | $-\underset{\underset{M_5}{\parallel}}{C}-CH_2-O-\text{(m-F-C}_6H_4)$ | H OCH₃ | 16-(m-fluorophenoxy)-17,18,-19,20-tetranor |
| 148 | $-\underset{\underset{M_5}{\parallel}}{C}-CH_2-O-\text{(m-F-C}_6H_4)$ | H OCH₃ | 15-epi-16-(m-fluorophenoxy)-17,18,19,20-tetranor |
| 149 | $-\underset{\underset{M_5}{\parallel}}{\underset{\mid}{C}}-\underset{\underset{CH_3}{\mid}}{\overset{CH_3}{C}}-O-\text{(m-F-C}_6H_4)$ | H OCH₃ | 16-methyl-16-(m-fluorophenoxy)-18,19,20-trinor |
| 150 | $-\underset{\underset{M_5}{\parallel}}{\underset{\mid}{C}}-\underset{\underset{CH_3}{\mid}}{\overset{CH_3}{C}}-O-\text{(m-F-C}_6H_4)$ | H OCH₃ | 15-epi-16-methyl-16-(m-fluorophenoxy)-18,19,20-trinor |
| 151 | $-\underset{\underset{M_5}{\parallel}}{C}-CH_2-O-\text{(p-F-C}_6H_4)$ | H OCH₃ | 16-(p-fluorophenoxy)-17,18,-19,20,tetranor |
| 152 | $-\underset{\underset{M_5}{\parallel}}{C}-CH_2-O-\text{(p-F-C}_6H_4)$ | H OCH₃ | 15-epi-16-(p-fluorophenoxy)-17,18,19,20-tetranor |
| 153 | $-\underset{\underset{M_5}{\parallel}}{\underset{\mid}{C}}-\underset{\underset{CH_3}{\mid}}{\overset{CH_3}{C}}-O-\text{(p-F-C}_6H_4)$ | H OCH₃ | 16-methyl-16-(p-fluorphenoxy)-18,19,20-trinor |
| 154 | $-\underset{\underset{M_5}{\parallel}}{\underset{\mid}{C}}-\underset{\underset{CH_3}{\mid}}{\overset{CH_3}{C}}-O-\text{(p-F-C}_6H_4)$ | H OCH₃ | 15-epi-16-methyl-16-(p-fluorophenoxy)-18,19,20-trinor |
| 155 | $-\underset{\underset{M_5}{\parallel}}{C}-CH_2-O-\text{(o-CF}_3\text{-C}_6H_4)$ | H OCH₃ | 16-o-trifluoromethylphenoxy)-17,18,19,20-tetranor |
| 156 | $-\underset{\underset{M_5}{\parallel}}{C}-CH_2-O-\text{(o-CF}_3\text{-C}_6H_4)$ | H OCH₃ | 15-epi-16-(o-trifluoromethylphenoxy)-17,18,-19,20-tetranor |
| 157 | $-\underset{\underset{M_5}{\parallel}}{\underset{\mid}{C}}-\underset{\underset{CH_3}{\mid}}{\overset{CH_3}{C}}-O-\text{(o-CF}_3\text{-C}_6H_4)$ | H OCH₃ | 16-methyl-16-(o-trifluoromethylphenoxy)-18,19,20-trinor |
| 158 | $-\underset{\underset{M_5}{\mid}}{\underset{\parallel}{Cl}}-\underset{\underset{CH_3}{\mid}}{\overset{CH_3}{C}}-O-\text{(o-CF}_3\text{-C}_6H_4)$ | H OCH₃ | 15-epi-16-methyl-16-o-trifluoromethylphenoxy)-18,19,-20-trinor |
| 159 | $-\underset{\underset{M_5}{\parallel}}{C}-CH_2-O-\text{(m-CF}_3\text{-C}_6H_4)$ | H OCH₃ | 16-(m-trifluoromethylphenoxy)-17,18,19,20-tetranor |
| 160 | $-\underset{\underset{M_5}{\parallel}}{C}-CH_2-O-\text{(m-CF}_3\text{-C}_6H_4)$ | H OCH₃ | 15-epi-16-(m-trifluoromethylphenoxy)-17,18,-19,20-tetranor |
| 161 | $-\underset{\underset{M_5}{\parallel}}{\underset{\mid}{C}}-\underset{\underset{CH_3}{\mid}}{\overset{CH_3}{C}}-O-\text{(m-CF}_3\text{-C}_6H_4)$ | H OCH₃ | 16-methyl-16-(m-trifluoromethylphenoxy)-18,19,20-trinor |
| 162 | $-\underset{\underset{M_5}{\parallel}}{\underset{\mid}{C}}-\underset{\underset{CH_3}{\mid}}{\overset{CH_3}{C}}-O-\text{(m-CF}_3\text{-C}_6H_4)$ | H OCH₃ | 15-epi-16-methyl-16-(m-trifluoromethylphenoxy)-18,19,-20-trinor |
| 163 | $-\underset{\underset{M_5}{\parallel}}{C}-CH_2-O-\text{(p-CF}_3\text{-C}_6H_4)$ | H OCH₃ | 16-(p-trifluoromethylphenoxy)-17,18,19,20-tetranor |
| 164 | $-\underset{\underset{M_5}{\parallel}}{Cl}-CH_2-O-\text{(p-CF}_3\text{-C}_6H_4)$ | H OCH₃ | 15-epi-16-(p-trifluoromethylphenoxy)-17,18,-19,20-tetranor |
| 165 | $-\underset{\underset{M_5}{\parallel}}{\underset{\mid}{C}}-\underset{\underset{CH_3}{\mid}}{\overset{CH_3}{C}}-O-\text{(p-CF}_3\text{-C}_6H_4)$ | H OCH₃ | 16-methyl-16-(p-trifluoromethylphenoxy)-18,19,20-trinor |
| 166 | $-\underset{\underset{M_5}{\parallel}}{\underset{\mid}{C}}-\underset{\underset{CH_3}{\mid}}{\overset{CH_3}{C}}-O-\text{(p-CF}_3\text{-C}_6H_4)$ | H OCH₃ | 15-epi-16-methyl-16-(m-trifluoromethylphenoxy)-18,19,-20-trinor |

Example 167

15-Methyl-16-phenoxy-17,18,19,20-tetranor-PGE$_2$, Methyl Ester (Formula IV: R$_1$ is methyl, R$_4$ and R$_5$ are hydrogen, M$_3$ is

g is 3, and s is zero).

A. The compound of Example 1, 15-methyl-16-phenoxy-17,18,19,20-tetranor-PGF$_{2\alpha}$ methyl ester is transformed into its 11-(trimethylsilyl)ether. N-trimethylsilyldiethylamine (1.7 ml.) is added slowly to a mixture of the compound of Example 1 (0.46 g.) and 15 ml. of acetone previously cooled to 31 48° C., and kept under nitrogen. Progress of the reaction is monitored by thin layer chromatography. The reaction temperature is maintained at about −45° C. to −35° C. for 1.5 hours whereupon the mixture is diluted with about 91 ml. of diethyl ether (previously cooled to −78° C.). The solution is washed with 91 ml. of cold saturated sodium bicarbonate solution, and the aqueous phase is washed with ether. The ether extract and washings are washed with brine, dried over sodium sulfate and concentrated to yield the 11-(trimethylsilyl)ether (0.5 g.).

B. A solution of the product of step A of this example (0.66 g.) in 6 ml. of dichloromethane is added to Collins reagent, prepared from chromium trioxide (1.3 g.) and pyridine (2.1 ml.) in 61 ml. of dichloromethane and cooled to 0° C. The mixture is stirred at 0° C. for 5 min. and then at about 25° C. for 10 min., and filtered. The filtrate is concentrated to yield the corresponding PGE$_2$-type, 11-(trimethylsilyl)ether (0.6 g.).

C. A solution of the compound of part B of this example (about 0.6 g.) in 33 ml. of methanol is mixed with 16 ml. of water and about 1.6 ml. of acetic acid at about 25° C. is stirred for about 15 min. The mixture is partitioned between diethyl ether and 0.2 M sodium hydrogen sulfate. The ether extract is washed with saturated aqueous sodium bicarbonate, then with brine, dried over sodium sulfate and concentrated to a product containing the title compound of the example (0.46 gm).

The product is subjected to chromatography on silica gel, packed with 75% ethyl acetate in hexane, eluting with ethyl acetate. Those fractions containing the title compound free of starting material and impurities are combined and concentrated to yield the title compound 257 mg.

NMR absorptions are observed at 1.43, 3.63, 3.88, 1.20–4.22, 5.23–5.53, 5.72–5.92, and 6.75–7.55. Infrared absorptions are observed at 3440, 2940, 2920, 2860, 1740, 1600, 1585, 1495, 1455, 1435, 1245, 1170, 1160, 1080, 1045, 975, 755, 735, and 695 cm$^{-1}$. The mass spectrum shows base peak absorption at 560.2947 and other peaks at 560, 545, 529, 470, 453 and 309.

Following the procedure of Example 167, but replacing 15-methyl-16-phenoxy-17,18,19-tetranor-PGF$_{2\alpha}$ methyl ester with its 15-epimer, the corresponding product is prepared, NMR absorptions are observed at 1.43, 3.63, 3.90, 1.17–4.23, 5.22–5.57, 5.72–5.90, and 6.77–7.57 δ.

Further following the procedure of Example 167, but replacing the title compound with each of the various 15α or 15β-15-methyl-PGF$_{2\alpha}$-type compounds of Examples 2 through 84, there are obtained the corresponding PGE$_2$-type compounds. The compounds thus obtained are in either the free acid or methyl ester form. Accordingly, there are obtained the following 15-methyl compounds of either the 15α or 15β configuration, with either the natural carboxy terminated chain length or 2 additional carbon atoms in the carboxy terminated chain length, e.g. 2a,2b-dihomo-PG-type compounds, as described in Examples 2 through 84. These compounds comprise Examples 168–246.

Example 247
16-Phenoxy-17,18,19,20-tetranor-PGE$_2$, Methyl Ester, 15-Methyl Ether (Formula IV: R$_1$ is methyl, R$_4$ and R$_5$ are hydrogen, M$_3$ is

g is 3, and s is zero).

A. Following the procedure of Example 167, part A, but using as starting material 16-phenoxy-17,18,19,20-tetranor-PGF$_{2\alpha}$, methyl ester 15-methyl ether, the 11-silyl ether derivative of the starting material is prepared.

B. Following the procedure of Example 167, part B, the 9-hydroxy group of the product of part A of this example is transformed into a 9-oxo group. Accordingly, 16-phenoxy-17,18,19,20-tetranor-PGE$_2$, methyl ester, 11-silyl ether, 15-methyl ether is prepared.

C. Following the procedure of Example 167, part C, the 11-silyl ether compound of part B of this example is hydrolyzed to yield the title compound.

Following the procedure of Example 247, but using as starting material the 15-methyl ether compounds of Examples 85–166 there are accordingly prepared 15α- or 15β-15-methyl ethers in either free acid or ester form, having carboxy terminated chain lengths of either 7 or 9 carbon atoms. There are accordingly prepared PGE$_2$-type compounds comprising Examples 248–326.

Example 327
15-Methyl-16-phenoxy-PGE$_1$, Methyl Ester (Formula V: wherein R$_1$ is methyl, R$_4$ and R$_5$ are hydrogen, M$_3$ is

g is 3, and s is zero).

The compound of Example 167, 15-methyl-16-phenoxy-17,18,19,20-tetranor-PGE$_2$, methyl ester (0.6 g.), 5 percent rhondium-on-alumina catalyst (40 mg.), and 16 ml. of ethyl acetate is stirred under one atmosphere of hydrogen at about 0° C. until substantially all of the starting material has been used, as shown by thin layer chromatography. The mixture is filtered to remove catalysts and the filtrate is concentrated. The residue is chromatographed to yield the title compound.

Example 328
16-Phenoxy-17,18,19,20-tetranor-PGE$_1$, Methyl Ester, 15-Methyl Ether (Formula V: R$_1$ is methyl, R$_4$ and R$_5$ are hydrogen, M$_3$ is

g is 3, and s is zero).

Following the procedure of Example 327, but using as starting material the compound of Example 247, 16-phenoxy-17,18,19,20-tetranor-PGE$_2$, methyl ester 15-methyl ether, there is prepared the title compound of this example.

Following the procedure of Example 327 or 328, but using as starting material the PGE$_2$-type compounds of Examples 168–246 or 248–326 there are prepared the corresponding PGE$_1$-type compounds.

Example 329
15-Methyl-16-phenoxy-17,18,19,20-tetranor-13,14-dihydro-PGE$_1$, Methyl Ester (Formula VI: R$_1$ is methyl, R$_4$ and R$_5$ are hydrogen, M$_3$ is

g is 3 and s is zero).

A solution of the compound of Example 167, 15-methyl-16-phenoxy-17,18,19,20-tetranor-PGE$_2$, methyl ester (100 mg. in 10 ml. of ethyl acetate is shaken with hydrogen at atmosphere pressure at 25° C. in the presence of a 5 percent palladium-on-charcoal catalyst (15 mg.). Two equivalents of hydrogen are used, whereupon the hydrogenation is stopped and the catalyst is removed by filtration. The filtrate is concentrated under reduced pressure and the residue is chromatographed on silica gel, and fractions containing pure product concentrated to give the title compound.

Following the procedure of Example 329, but using as starting material the 15-methyl-PGE$_2$-type compounds of Examples 168–247 there are prepared the corresponding 13,14-dihydro-PGE$_1$ compounds in either free acid or ester form.

Example 330
16-Phenoxy-17,18,19,20-tetranor-13,14-dihydro-PGE$_1$, Methyl Ester, 15-Methyl Ether (Formula VI: R$_1$ is methyl, R$_4$ and R$_5$ are hydrogen, M$_3$ is

g is 3, and s is zero).

Following the procedure of Example 329, but using as starting material the compound of Example 247, 16-phenoxy-17,18,19,20-tetranor-PGE$_2$, methyl ester 15-methyl ether, there is prepared the title compound of this example.

Following the procedure of Example 330, but using as starting material the compound of Examples 248–326, there are prepared the corresponding 13,14-dihydro-PGE$_1$-type, 15-methyl ether compounds in either their free acid or methyl ester form.

Example 331
15-Methyl-16-phenoxy-17,18,19,20-tetranor-PGF$_{2\beta}$, Methyl Ester (Formula I: ∼ is alpha, R$_1$ is methyl, R$_4$ and R$_5$ are hydrogen, M$_3$ is

g is 3, and s is zero).

Refer to Chart I. A solution of sodium borohydride 300 mg. in 6 ml. of ice-cold methanol is added to a solution of 15-methyl-16-phenoxy-17,18,19,20-tetranor-PGE$_2$, methyl ester (Example 167, 650 mg.) in 30 ml. of methanol at −20° C. The mixture is stirred for an additional 5 minutes, made slightly acidic with acetic acid and concentrated under reduced pressure. The residue is extracted with dichloromethane and the organic phase is washed with water, chloride, and brine, then dried over sodium sulfate, and concentrated under reduced pressure.

This residue is chromatographed over silica gel wet packed in ethyl acetate, eluting with 2 percent, 4 percent, 7.5 percent, and 10 percent ethanol in ethyl acetate. Those fractions containing the title compound free from starting material and impurities as shown by TLC, are combined and concentrated to yield the title compound of this example or its corresponding PGF$_{2\alpha}$-type compound.

Following the procedure of Example 331, but using as starting material the 15-alkyl-PGE$_2$-type compounds of Examples 168 through 246 there are prepared the corresponding 15-methyl-PGF$_{2\beta}$- or PGF$_{2\alpha}$-type compounds.

Following the procedure of Example 331, but using as starting material either the 15-methyl-PGE$_1$-type compounds described in Example 327 and the paragraph following Example 327 or the 15-methyl-13,14-dihydro-PGE$_1$-type compounds described in Example 329 and the paragraph following Example 329, there are prepared the corresponding 15-methyl-PGF$_{1\beta}$- or PGF$_{1\alpha}$- or 13,14-dihydro-PGF$_{1\beta}$- or PGF$_{1\alpha}$-type compounds.

Example 332
16-Phenoxy-17,18,19,20-tetranor-PGF$_{2\beta}$, Methyl Ester 15-Methyl Ether (Formula I: ∼ is beta, R$_1$ is methyl, R$_4$ and R$_5$ are hydrogen, M$_3$ is

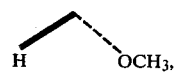

g is 3, and s is zero).

Following the procedure of Example 331, but using as starting material the compound of Example 247, 16-phenoxy-17,18,19,20-tetranor-PGE$_2$, methyl ester, 15-methyl ether, there is prepared the compound of this example or its 9α-isomer.

Following the procedure of Example 332, but using as starting materials the PGE$_2$-type, 15-methyl ether compounds of Examples 248–326 there are prepared the corresponding PGF$_{2\beta}$- or PGF$_{2\alpha}$-type, 15-methyl ether compounds.

Following the procedure of Example 332, but using as starting material either the PGE$_1$-type, 15-methyl ether compounds described in Example 328 and the paragraph following Example 328, or the 13,14-dihydro-PGE$_1$-type, 15-methyl ether compounds described in Example 330 or in the text following Example 330 there are prepared the corresponding PGF$_{1\beta}$- or PGF$_{1\alpha}$-type, 15-methyl ether or 13,14-dihydro-PGF$_{1\beta}$- or PGF$_{2\alpha}$-type, 15-methyl ether compounds.

Example 333
15-Methyl-16-phenoxy-17,18,19,20-tetranor-PGA$_2$, Methyl Ester (Formula X: R$_1$ is methyl, R$_4$ and R$_5$ are hydrogen, M$_3$ is

g is 3, and s is zero).

Refer to Chart I. A solution of the compound of Example 167, 15-methyl-16-phenoxy-17,18,19,20-tetranor-PGE$_2$, methyl ester (300 mg.), 4 ml. of tetrahydrofuran and 4 ml. 0.5 N hydrochloric acid is left standing at 25° C. for 5 days. Brine and dichloromethane-ether (1:3) are added and the mixture is stirred. The organic phase is separated, dried, and concentrated. The residue is dissolved in ether and the solution is extracted with saturated aqueous sodium bicarbonate. This aqueous phase is acidified with dilute hydrochloric acid and then extracted with dichloromethane. Alternatively pure product is obtained by silica gel chromatography purification of the residue.

Following the procedure of Example 333 but using as starting material the 15-methyl-PGE$_2$-type compounds of Examples 168–246, there are prepared the corresponding 15-methyl-PGA$_2$-type compounds.

Following the procedure of Example 333, but using as starting material either the 15-alkyl-PGE$_1$-type compounds of Example 327 or the paragraph following Example 327, or the 15-methyl-13,14-dihydro-PGE$_1$-type compounds of Example 329 or the paragraph following Example 329, there are prepared corresponding 15-methyl-PGA$_1$ or 13,14-dihydro-PGA$_1$-type compounds of this invention.

Example 334
16-Phenoxy-17,18,19,20-tetranor-PGA$_2$, Methyl Ester 15-Methyl Ester (Formula X: R$_1$ is methyl, R$_4$ and R$_5$ are hydrogen, M$_3$ is

g is 3, and s is zero).

Following the procedure of Example 333, but using as starting material the compound of Example 86, 16-phenoxy-17,18,19,20-tetranor-PGF$_2$, methyl ester 15-methyl ether, the title compound of this example is prepared.

Following the procedure of Example 334, but using as starting material the PGE$_2$-type, 15-methyl ether compounds of Examples 248–326, there are prepared the corresponding PGA$_2$-type, 15-methyl ether type compounds of this invention.

Following the procedure of Example 334, but using as starting material either the PGE$_1$-type, 15-methyl ether compounds of Example 328 or the paragraph following Example 328 or the 13,14-dihydro-PGE$_1$-type, 15-methyl ether compounds of Example 330 or the paragraph following Example 330, there are prepared corresponding PGA$_1$-type, 15-methyl ether or 13,14-dihydro-PGA$_1$-type, 15-methyl ether compounds of this invention.

Example 335
15-Methyl-16-phenoxy-17,18,19,20-tetranor-PGB$_2$, Methyl Ester (Formula VII: R$_1$ is methyl, R$_4$ and R$_5$ are hydrogen, M$_3$ is

g is 3, and s is zero).

Refer to Chart I. A solution of 15-methyl-16-phenoxy-17,18,19,20-tetranor-PGE$_2$ (Example 167, 200 mg.) in 100 ml. of 50 percent aqueous ethanol containing about 1 g. of potassium hydroxide is kept at 25° C. for 10 hours under nitrogen. The solution is then cooled to 10° C., neutralized by the addition of 3 N hydrochloric acid at 10° C. The resulting solution is extracted repeatedly with ethyl acetate, combined with ethyl acetate extracts and are washed with water and then with brine, dried, and concentrated to yield the title compound.

Following the procedure of Example 335, but using as starting material the 15-methyl-PGE$_2$-type compounds of Examples 168–246 there are prepared the corresponding 15-methyl-PGB$_2$-type compounds of this invention.

Following the procedure of Example 335, but using as starting material either the 15-methyl-PGE$_1$-type compounds of Example 327 or the paragraph following Example 327 or the 15-methyl-13,14-dihydro-PGE$_1$-type compounds of Example 329 or the paragraph following Example 329, corresponding 15-methyl-PGE$_1$ or 13,14-dihydro-PGE$_1$-type compounds of this invention are prepared.

Example 336
16-Phenoxy-17,18,19,20-tetranor-PGB$_2$, Methyl Ester, 15-Methyl-Ether (Formula X: R$_1$ is methyl, R$_4$ and R$_5$ are hydrogen, M$_3$ is

g is 3 and s is zero).

Following the procedure of Example 335, but using as starting material the compound of Example 247, 16-phenoxy-17,18,19,20-tetranor-PGE$_2$, methyl ester 15-methyl ether, there is prepared the title compound of this invention.

Following the procedure of Example 336, but using as starting material the PGE$_2$-type, 15-methyl ether compounds of Examples 248–326, the corresponding PGB$_2$-type, 15-methyl ether compounds are prepared.

Following the procedure of Example 336, but using as starting material either the PGE$_1$-type, 15-methyl ether compounds of Example 328 or the paragraph following Example 328, or the 13,14-dihydro-PGE$_1$-type, 15-methyl ether compounds of Example 330 or the paragraph following Example 330, there are prepared corresponding PGB$_1$- and 13,14-dihydro-PGE$_1$-type, 15-methyl ether compounds of this invention.

Example 337
15-Methyl-16-phenoxy-17,18,19,20-tetranor-PGF$_{2\alpha}$, Sodium Salt (Formula I: ~ is alpha, R$_1$ is sodium, R$_4$ and R$_5$ are hydrogen, M is

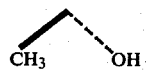

g is 3, and s is 0).

A solution of 15-methyl-16-phenoxy-17,18,19,20-tetranor-PGF$_{2\alpha}$ (Example 2, 100 mg.) in 50 ml. of water-ethanol mixture (1:1) is cooled to 5° C. and neutralized with an equivalent amount of 0.1 N aqueous sodium hydroxide solution. The neutral solution is concentrated to residue of the title compound.

Following the procedure of Example 337, but using potassium hydroxide, calcium hydroxide, the corresponding salts of 15-methyl-16-phenoxy-17,18,19,20-tetranor-PGF$_{2\alpha}$ are obtained.

Following the procedure of Example 337, but using as starting material the PGF$_\alpha$-, PGF$_\beta$-, PGA-, and PGB-type free acids of the examples hereinabove, there are obtained corresponding sodium, potassium, calcium, trimethyl ammonium, and benzyl trimethyl ammonium salts thereof.

Example 338
p-Acetamidophenyl Ester of 15-Methyl-16-phenoxy-17,18,19,20-tetranor-PGF$_{2\alpha}$.

A solution of 15-methyl-16-phenoxy-17,18,19,20-tetranor-PGF$_{2\alpha}$, the compound of Example 2, in acetone is treated at −10° C. with twice the stoichiometric amount of triethylamine as PG analog, and is treated with an equal quantity of isobutylchloroformate, whereupon triethylamine hydrochloride is precipitated. After 5 minutes the mixture is treated with several fold stoichiometric excess (over the prostaglandin analog) of p-acetamidophenol in pyridine for 3 hours at 25° C. The solvent is removed under reduced pressure and the residue is taken up in acetonitrile and again concentrated. The crude residue is subjected to silica gel chromatography, eluting with ethyl acetate and methanol (90:10). The residue obtained by concentration of selected fractions, is the title compound of this example.

Following the procedure of Example 338, but using in place of the prostaglandin analog any of the free acid PGF$_\alpha$-, PGF$_\beta$-, PGA-, PGB- or PGE-type compounds of this invention, there are prepared the corresponding p-acetamidophenol esters.

Following the procedure of Example 338 and using any of the prostaglandin-type free acids described in the previous paragraph, and using, in place of p-acetamidophenol, a phenol or naphthol selected from the group consisting of p-(p-acetamidobenzamido)phenol, p-benzamidophenol, p-hydroxyphenylurea, p-hydroxybenzaldehydesemi-carbazone, and 2-naphthol, the corresponding substituted phenyl or naphthyl esters are obtained.

Example 339
15-Methyl-16-phenoxy-17,18,19,20-tetranor-PGF$_{2\alpha}$, Methyl Ester, or its 15-epimer.

A. To a stirred solution of 26.3 gm. of the reaction product of Preparation 4, part B in 398 ml. of dry toluene under nitrogen at $-78°$ C. is added 150 ml. of 20% diisobutylaluminum hydride in hexane. After one hour an additional 150 ml. of the above hexane solution is added. After 15 hours the reaction is quenched by addition of 750 ml. of saturated ammonium chloride. After warming, the reaction product is filtered, washed with ethyl acetate and water, and the organic extracts, then washed with brine, dried, and concentrated (employing a benzene azeotrope) to yield 27.7 g. of lactol.

B. A mixture of 24.4 g. of 50% sodium hydride in mineral oil and 818 ml. of dimethylsulfoxide is stirred under nitrogen at 70° C. After one hour and cooling to 15° C. (4-carboxybutyl)triphenylphosphonium bromide is added.

Thereafter 27.7 g. of the lactol of part A is added, monitoring the progress of the reaction with thin layer chromatography. On completion, the reaction mixture is quenched by addition of 1.2 l. of 2M sodium bisulfate, diethyl ether, and ice water. The resulting mixture is extracted with diethyl ether, and thereafter the organic extract is extracted with 200 ml. of 1N sodium hydroxide, and water. The basic aqueous extract above is then extracted with diethyl ether, and all organic extracts then combined and concentrated to yield 22 g. of an oil.

C. The crude product (part B) is then esterified by dissolving this product in ether and methanol (1:1) and treating with excess diazomethane. The resulting solution is then concentrated under reduced pressure yielding 22 gm. of an oil.

D. Crude product from part C, above, is chromatographed on silica gel, eluting with ethyl acetate and Skellysolve B (isomeric hexanes) yielding 10.9 gm. of pure 15(RS) product. Then, 9.0 gm. of the pure 15(RS) product are subjected to high pressure liquid chromatographic separation, eluting with 30% acetone in dichloromethane, at a flow rate of 6 ml/min. The title compound is obtained in a yield of 0.67 gm. and the 15-epi compound in a yield of 0.56 gm.

Title compound shows mass spectral base peak at 634.3541 and other peaks at 634, 619, 603, 544, 527, 513, 437, and 217. NMR absorptions are observed at 1.38, 3.62, 3.83, 3.57–4.47, 5.07–5.82, and 6.75–7.67 δ. Infrared absorption is observed at (cm$^{-1}$) 3400, 3060, 3000, 1735, 1600, 1585, 1500, 1455, 1430, 1370, 1300, 1290, 1245, 1170, 1155, 1120, 1080, 1045, 875, 755, and 690.

The 15-epimer shows mass spectral base peak absorption at 527.3044 and other peaks at 634, 619, 544, 527, 455, 437, and 217. NMR absorptions are observed at 1.38, 1.32–3.28, 3.63, 3.85, 3.60–4.35, 5.20–5.83, and 6.72–7.65 δ.

I claim:
1. A compound of the formula:

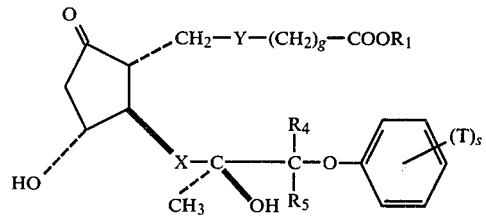

or the mixture comprising that compound and the enantiomer thereof, wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to four carbon atoms, inclusive, a pharmacologically acceptable cation,

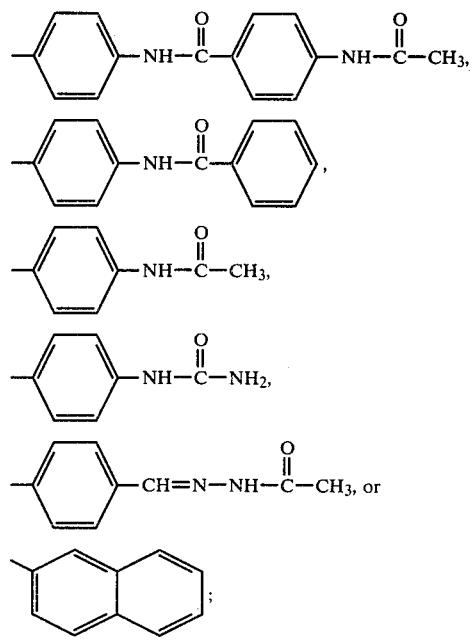

wherein T is chloro, fluoro, trifluoromethyl, alkyl of one to 3 carbon atoms, inclusive, or —OR$_2$, wherein R$_2$ is alkyl of one to 3 carbon atoms, inclusive, and s is zero, one, 2, or 3, with the proviso that not more than two T's are other than alkyl, the various T's being the same or different;

wherein (a) X is trans-CH=CH— and Y is cis-CH=CH— or —CH$_2$CH$_2$— or (b) X and Y are both —CH$_2$CH$_2$—;

wherein g is 3 to 5, inclusive; and wherein R$_4$ and R$_5$ are hydrogen or alkyl of one or 2 carbon atoms, inclusive, being the same or different.

2. A compound according to claim 1, wherein X is trans-CH=CH— and Y is —CH$_2$CH$_2$—.

3. A compound according to claim 1, wherein X and Y are —CH$_2$CH$_2$—.

4. A compound according to claim 1, wherein X is trans-CH=CH— and Y is cis-CH=CH—.

5. A compound according to claim 4, wherein g is 5.

6. A compound according to claim 5, wherein R$_4$ and R$_5$ are both hydrogen.

7. A compound according to claim 6, wherein T is chloro, fluoro, or trifluoromethyl and s is zero or one.

8. 2a,2b-Dihomo-15-epi-15-methyl-17,18,19,20-tetranor-PGE$_2$, methyl ester, a compound according to claim 7.

9. A compound according to claim 4, wherein g is 3.

10. A compound according to claim 9, wherein R$_4$ and R$_5$ are both methyl.

11. A compound according to claim 10, wherein T is chloro, fluoro, trifluoromethyl, and s is zero or one.

12. 15-epi-15,16-Dimethyl-16-phenoxy-18,19,20-trinor-PGE$_2$, methyl ester, a compound according to claim 11.

13. A compound according to claim 9, wherein R$_4$ and R$_5$ are hydrogen.

14. A compound according to claim 13, wherein T is chloro, fluoro, or trifluoromethyl and s is zero or one.

15. 15-epi-15-Methyl-16-phenoxy-17,18,19,20-tetranor-PGE$_2$, methyl ester, a compound according to claim 14.

16. 15-epi-15-Methyl-16-(m-chlorophenoxy)-17,18,19,20-tetranor-PGE$_2$, methyl ester, a compound according to claim 14.

17. 15-epi-15-Methyl-16-(p-fluorophenoxy)-17,18,19,20-tetranor-PGE$_2$, methyl ester, a compound according to claim 14.

18. 15-epi-15-Methyl-16-(m-trifluoromethylphenoxy)-17,18,19,20-tetranor-PGE$_2$, methyl ester, a compound according to claim 14.

* * * * *

UNITED STATES PATENT OFFICE
CERTIFICATE OF CORRECTION

Patent No. 4,154,950        Dated  15 May 1979

Inventor(s)  Norman A. Nelson

It is certified that error appears in the above-identified patent and that said Letters Patent are hereby corrected as shown below:

Column 14, line 4, "PGE-thype" should read -- PGE-type --; line 46, "described above the the PGE" should read -- described above for the PGE --;

Column 15, line 32, "invention by hydrogen" should read -- invention be hydrogen --;

Column 31, lines 46-53, and lines 55-62, that portion of Formulas XXXVIII and XXXIX reading

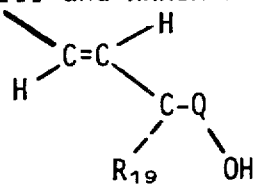         should read         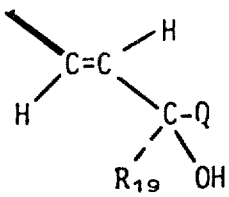

Column 42, line 29, "for examply" should read -- for example --;

Column 67, line 43, "the 3α-methoxy lactol" should read -- the 3β-methoxy lactol --; lines 65-68,

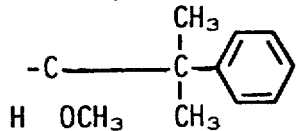         should read         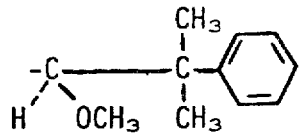

Columns 70, 71, and 73, in the column headings "M" should read -- $M_5$ --;

Column 70, lines 13-14, "16-methyl-16-20-phenoxy-18,19,trinor" should read -- 16-methyl-16-phenoxy-18,19,20-trinor --;

UNITED STATES PATENT OFFICE
CERTIFICATE OF CORRECTION

Patent No. 4,154,950     Dated 15 May 1979

Inventor(s) Norman A. Nelson

It is certified that error appears in the above-identified patent and that said Letters Patent are hereby corrected as shown below:

Column 72, line 57, "cooled to 31 48° C" should read -- cooled to 48° C --

Column 73, line 30, "15-methyl-16-phenoxy-17,18,19-tetranor-$PGF_2\alpha$" should read -- 15-methyl-16-phenoxy-17,18,19,20-tetranor-$PGF_2\alpha$ --;

Column 81, line 13, "2a,2b-Dihomo-15-epi-15-methyl-17,18,19,20-" should read -- 2a,2b-Dihomo-15-epi-15-methyl-16-phenoxy-17,18,19,20- --.

Signed and Sealed this

Eighth Day of September 1981

[SEAL]

Attest:

GERALD J. MOSSINGHOFF

Attesting Officer     Commissioner of Patents and Trademarks